US005998600A

United States Patent [19]

Barker et al.

[11] Patent Number: 5,998,600

[45] Date of Patent: Dec. 7, 1999

[54] β-CATENIN, TCF-4, AND APC INTERACT TO PREVENT CANCER

[75] Inventors: Nick Barker, Utrecht; Hans Clevers, Huis ter Heide, both of Netherlands; Vladimar Korinek, Prague, Czech Rep.

[73] Assignee: Utrecht University, The Netherlands

[21] Appl. No.: 09/003,687

[22] Filed: Jan. 7, 1998

Related U.S. Application Data

[62] Division of application No. 08/821,355, Mar. 20, 1997, Pat. No. 5,851,775.

[51] Int. Cl.[6] .................... C12N 15/12

[52] U.S. Cl. .................... 536/23.5; 536/23.1

[58] Field of Search .................... 536/23.1, 23.5

[56] References Cited

PUBLICATIONS

J. Castrop et al. "A Gene Family of HMG–box transcription factors with homology to tcf–1" Nucleic Acid Research, vol. 20, No. 3, 1992, p. 611.

L. Hillier et al. "The WashU–Merck EST Project" EMBL Sequence Data Library, Sep. 6, 1996.

J. Castrop et al. "A Gene Family of HMG–box transcription factors with homology to tcf–1", EMBL Sequence Data Library, Nov. 22, 1993.

K.W. Kinzler and B. Vogelstein, "Lessons from hereditary colorectal cancer", Cell, vol. 87, Oct. 18, 1996, pp. 159–170.

M. Molenaar et al. "XTcf–3 transcription factor mediates beta–catenin–induced axis formation in xenopus embryos" Cell, vol. 86, Aug. 1996, pp. 391–399.

M. Van De Wetering et al. "Identification and cloning of TCF–1, a t lymphocyte–specific transcription factor containing a sequence–specific hmg–bo+" The EMBO Journal, vol. 10, No. 1, 1991, pp. 123–132.

J. Behrens et al. "Functional interaction of bta–catenin with the transcription factor LEF–1" Nature, vol. 382, 1996, pp. 638–642.

V. Korinek et al. "Constitutive transcriptional activation by a beta–catenin–Tcf complex in APC–/–colon carcinoma" Science, vol. 275, Mar. 21, 1997, pp. 1784–1787.

H. Clevers and M. Van De Wetering, "TCF/LEF factors earn their wings" Trends in Genetics, vol. 13, No. 12, Dec. 1997, pp. 485–489.

Curt Suplee, The Washington Post, Key Process In Cancer Is Identified, Finding May Facilitate Early Detection, Therapy, 2–4 (1997).

Bonnee Rubinfeld et al. The Journal of Biological Chemistry, "The APC Protein and E–cadherin Form Similar but Independent Complexes with α–Catenin, β–Catenin, and Plakoglobin", vol. 270, No. 10, pp. 5549–5555 (1995).

J. Kawanishi et al., Molecular and Cellular Biology, "Loss of E–Cadherin–Dependent Cell–Cell Adhesion due to Mutation of the β–Catenin Gene in a Human Cancer Cell Line, HSC–39" vol. 15, No. 3, pp. 1175–1181 (1995).

P.F. Robins, J. Exp. Med., "A Mutated β–Catenin Gene Encodes a Melanoma–specific Antigen Recognized by Tumor Infiltrating Lymphocytes", vol. 183, pp. 1185–1192 (1996.

B. Rubinfeld et al., Science, "Association of the APC Gene Product with β–Catenin", vol. 262, pp. 1731–1734 (1993).

L.K. Su et al., Science, "Association of the APC Tumor Suppressor Protein with Catenins", vol. 262, pp. 1734–1737 (1993).

Bonnee Rubinfeld et al., Science, "Binding of GSK3β to the APC–β–Catenin Complex and Regulation of Complex Assembly", vol. 272, pp. 1023–1026 (1996).

Susan Munemitsu et al., Proc. Natl. Acad. Sci., "Regulation of intracellular β–catenin levels by the adenomatous polyposis coli (APC) tumor–suppressor protein", vol. 92, pp. 3046–3050 (1995).

Jurgen Behrens et al., Nature, "Functional interaction of β–catenin with the transcription factor LEF–1" vol. 382, pp. 638–642 (1996).

Otmar Huber et al., Mech. Dev., "Nuclear localization of β–catenin by interaction with transcription factor LEF–1", vol. 59, pp. 3–10 (1996).

Korinek et al. (1997) GenBank, Accession No. Y11306, Aug. 14, 1997, accessed Aug. 24, 1998.

*Primary Examiner*—Nancy Degen
*Assistant Examiner*—Robert Schwartzman
*Attorney, Agent, or Firm*—Banner & Witcoff, Ltd.

[57] ABSTRACT

The APC tumor suppressor protein binds to β-catenin, a protein recently shown to interact with Tcf/Lef transcription factors. Here, the gene encoding a Tcf family member that is expressed in colonic epithelium (hTcf-4) a was cloned and characterized. hTcf-4 transactivates transcription only when associated with β-catenin. Nuclei of $APC^{-/-}$ colon carcinoma cells were found to contain a stable β-catenin-hTCF-4 complex that was constitutively active, as measured by transcription of a Tcf reporter gene. Reintroduction of APC removed β-catenin from hTcf4 and abrogated the transcriptional transactivation. Constitutive transcription of TCF target genes, caused by loss of APC function, may be a crucial event in the early transformation of colonic epithelium. It is also shown here that the products of mutant APC genes found in colorectal tumors are defective in regulating β-catenin/Tcf-4 transcrpitional activation. Furthermore, colorectal tumors with intact APC genes were shown to contain subtle activating mutations of β-catenin that altered functionally significant phosphorylation sites. These results indicate that regulation of β-catenin is critical to APC's tumor suppressive effect and that this regulation can be circumvented by mutations in either APC or β-catenin.

2 Claims, 13 Drawing Sheets

FIG. 1A hTCF-4E hTCF-1E

```
1     M P Q L   N G G G         G D D L G A N D E L I S F K D E G   E Q E E K   S S E
      | | | |     | | |         | | | | | |   | | | : : |   | | |   | | : : |
1     M P Q L D S G G G G A G R G D D L G A P D E L L A F Q D E G E E Q D D K N R D S

34    N S S A E R D L A D V K S S L V N E S E T N Q N S S S D S E A E R R P P P R S E
              | | | | | : : | | | | | | | | |           : :                 |     |
41    P V G P E R D L A E L K S S L V N E S E         G A A A G A G V P G P G V R V H

74    S F R D K S R E S L E E A A K R Q D G G L F K G P P Y P G Y P F I M I P D L T S
            :   :   | : |             |           |     |                 :     | :   | |
77    G E A E G A P E A L G R E H T S Q R L F P D K   L P E S L E D G L K A P E C T S

114   P Y L P N G S V S P T A R T Y L Q M K W P L L D V Q A G S L Q S R Q A L K D A R
                      |     |       |   | : : |           | |     |     |
116   G M Y K E T V Y S     A   F N L L M H Y P   P P S G A G     Q H P Q           P

154   S P S P A H I V S N K V P V V Q H P H H V H P L T P L I T Y S N E H F T P G N P
        |   |   |     : |           |   | |   |   |       |     |     | | |         |
145   Q P   P L H   K A N           Q P P H G V   P     Q L S L Y     E H F N S P H P
```

Figure 1B:
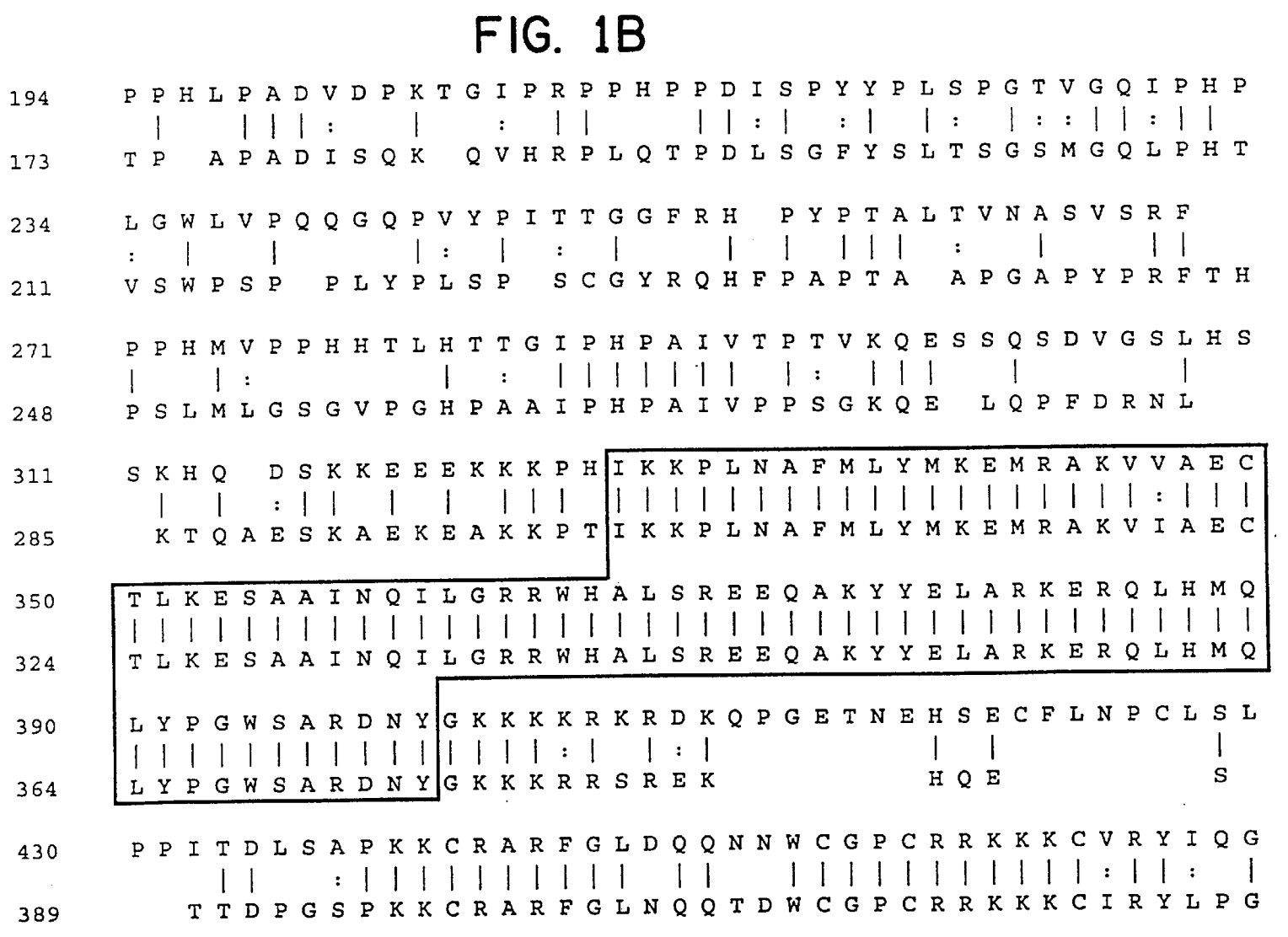

```
194 PPHLPADVDPKTGIPRPPHPPDISPYYPLSPGTVGQIPHP
173 TP APADISQK QVHRPLQTPDLSGFYSLTSGSMGQLPHT

234 LGWLVPQQGQPVYPITTGGFRH PYPTALTVNASVSRF
211 VSWPSP PLYPLSP SCGYRQHFPAPTA APGAPYPRFTH

271 PPHMVPPHHTLHTTGIPHPAIVTPTVKQESSQSDVGSLHS
248 PSLMLGSGVPGHPAAIPHPAIVPPSGKQE LQPFDRNL

311 SKHQ DSKKEEEKKKPHIKKPLNAFMLYMKEMRAKVVAEC
285 KTQAESKAEKEAKKPTIKKPLNAFMLYMKEMRAKVIAEC

350 TLKESAAINQILGRRWHALSREEQAKYYELARKERQLHMQ
324 TLKESAAINQILGRRWHALSREEQAKYYELARKERQLHMQ

390 LYPGWSARDNYGKKKKRKRDKQPGETNEHSECFLNPCLSL
364 LYPGWSARDNYGKKKRRSREK HQE S

430 PPITDLSAPKKCRARFGLDQQNNWCGPCRRKKKCVRYIQG
389 TTDPGSPKKCRARFGLNQQTDWCGPCRRKKKCIRYLPG
```

```
470   E G S C L S P P S S D G S L L D S P P P S P N L L G S P P R D A K S Q T E Q T Q
427   E G R C P S P V P S D D S A L   G C P G S P A P Q D S   P S Y H L L P R F P T E

510   P L S L S L K P D P   L A H L S   M M P P P P A L L L A E A T H K A S A L C P
465   L L T S P A E P A P T S P G L S T A L S L P T P G P P Q A P R S T L Q S T Q V Q

547   N G A L D L P P A A L Q P A A P S S S I A Q P S T S W L H S H S S L A G T Q P Q
505   Q Q E S Q R Q V A *

587   P L S L V T K S L E *
```

hTCF-4B hTCF-1B

```
390   L Y P G W S A R D N Y G K K K K R K R D K Q P G E T N G E K K S A F A T Y K V K
364   L Y P G W S A R D N Y G K K K R R S R E K H Q E S T T G G K R N A F G T Y P E K

430   A A A S A H P L Q M E A Y *
404   A A A P A P F L P M T V L *
```

β-CATENIN, TCF-4, AND APC INTERACT TO PREVENT CANCER

This is a divisional application of application Ser. No. 08/821,355, filed Mar. 20, 1997, U.S. Pat. No. 5,851,775.

The U.S. Government has a paid-up license in this invention and the right in limited circumstances to require the patent owner to license others on reasonable terms as provided for by the terms of grant CA57345 awarded by the National Institutes of Health.

TECHNICAL FIELD OF THE INVENTION

This invention is related to the field of cancer diagnostics and therapeutics. More particularly it relates to methods for diagnosing and treating cancers associated with APC or β-catenin mutations.

BACKGROUND OF THE INVENTION

Mutations of the adenomatous polyposis coli (APC) gene are the most common disease-causing genetic events in humans; approximately 50% of the population will develop colorectal polyps initiated by such mutations during a normal life span (14). Individuals who inherit APC mutations develop thousands of colorectal tumors, consistent with APC's tumor suppressor or "gatekeeping" role in colorectal tumorigenesis (15,16). APC homodimerizes through its amino-terminus (17), and interacts with at least six other proteins: β-catenin (18), γ-catenin (plakoglobin) (19), tubulin (20), EB1 (21), hDLG, a homologue of a Drosophila tumor suppressor protein (22), and ZW3/GSK3β kinase (23). Whether any of these interacting proteins communicate APC growth-controlling signals is unknown. Thus there is a need in the art for a fuller understanding of how the tumor suppressor gene APC functions in cells.

SUMMARY OF THE INVENTION

It is an object of the present invention to provide human nucleotide sequences encoding transcriptional activation proteins.

It is another object of the present invention to provide isolated preparations of transcriptional activation proteins.

It is an object of the present invention to provide methods of determining the presence or absence in a cell of wild-type APC or a downstream protein in the APC transcription regulatory pathway.

Another object of the invention is to provide methods of identifying candidate drugs for use in Familial Adenomatous Polyposis (FAP) patients or patients width increased risk of developing cancer, It is yet another object of the invention to provide methods of identifying candidate drugs for the treatment of cancer patients, in particular those with APC or β-catenin mutations.

Another object of the invention is to provide a method for diagnosing cancer in a sample suspected of being neoplastic.

Another object of the invention is to provide a method for treating a patient with colorectal cancer or other cancer associated with FAP.

These and other objects of the invention are achieved by providing one or more of the embodiments described below. In one embodiment of the invention an intron-free DNA molecule is provided which encodes Tcf-4 protein as shown in SEQ ID NO: 5 or 6.

According to another embodiment of the invention an isolated Tcf-4 protein is provided. The protein is substantially free of other human proteins, and has a sequence as shown in SEQ ID NO: 5 or 6.

In another embodiment of the invention a method is provided for determining the presence or absence in a cell of wild-type APC or a downstream protein in the APC transcription regulatory pathway. The method comprises the steps of:

- introducing a Tcf-responsive reporter gene into the cell; and
- measuring transcription of said reporter gene; wherein a cell which supports active transcription of said reporter gene does not have wild-type APC or does not have a wild-type downstream protein in the APC transcription regulatory pathway.

According to yet another embodiment of the invention a method is provided for determining the presence or absence in a cell of wild-type APC. The method comprises the steps of:

- contacting a Tcf-responsive reporter gene with a lysate of the cell; and
- measuring transcription of said reporter gene; wherein a lysate which inhibits said transcription has wild-type APC.

In still another embodiment of the invention a method of identifying candidate drugs is provided. The drugs may be useful for treatment of FAP or other cancer patients or patients with increased risk of developing cancer.

The method comprises the steps of:

- contacting a cell having no wild-type APC or a mutant β-catenin with a test compound;
- measuring transcription of a Tcf-responsive reporter gene, wherein a test compound which inhibits the transcription of the reporter gene is a candidate drug for cancer therapy.

According to yet another aspect of the invention another method is provided for identifying candidate drugs for use in for use in FAP patients, colon cancer patients, patients with mutations in β-catenin or APC, or patients with increased risk of developing cancer. The method, comprises the steps of:

- contacting a Tcf-responsive reporter gene with a test compound under conditions in which the reporter gene is transcribed in the absence of the test compound; and
- measuring transcription of the Tcf-responsive reporter gene; wherein a test compound which inhibits said transcription is a candidate drug for cancer therapy.

According to another aspect of the invention a method is provided for identifying candidate drugs for use in FAP patients or patients with increased risk of developing cancer. The method comprises the steps of:

- contacting a test compound with β-catenin and Tcf-4 under conditions in which β-catenin and Tcf-4 bind to each other; and
- determining whether the test compound inhibits the binding of β-catenin and Tcf-4, a test compound which inhibits the binding being a candidate for cancer therapy or prophylaxis.

According to still another embodiment of the invention a method is provided for diagnosing cancer in a sample suspected of being neoplastic. The method comprises the steps of:

- comparing a CTNNB sequence found in the sample to a second CTNNB sequence found in a normal tissue, wherein a difference between the first and second sequence is an indicator of cancer.

According to another aspect of the invention a method is provided for treating a patient with colorectal cancer or other cancer associated with FAP.

The method comprises the step of:

administering to the patient a nucleotide sequence comprising a portion of the APC coding sequence, said portion consisting of the β-catenin binding site.

According to another aspect of the invention a method is provided for treating a patient with colorectal cancer or other cancer associated with FAP.

The method comprises the step of:

administering to the patient a polypeptide comprising a portion of the APC coding sequence, said portion consisting of the β-catenin binding site.

The present invention thus provides the art with diagnostic, therapeutic and drug discovery methods especially useful for FAP and other cancers with APC or β-catenin mutations.

BRIEF DESCRIPTION OF THE DRAWINGS

FIGS. 1A–1B. Sequence comparison of hTcf-4 and hTcf-1.

Two alternative splice forms of hTcf-4 were identified, each encoding a different COOH-terminus. One form (hTcf-4E SEQ ID NO:6) was homologous to hTCF-1E, (SEQ ID NO:9) FIG. 1A (7); the other form (hTcf-4B, SEQ ID NO:5), was homologous to hTcf-1B, SEQ ID NO:8, (FIG. 1B). The highly conserved $NH_2$-terminal interaction domain and the High Mobility Group (HMG) box DNA-binding region are boxed. Abbreviations for the amino acids are: A. Ala; C, Cys; D, Asp; E, Glu; F, Phe; G, Gly; H, His; I, Ile; IC, Lys; L, Leu; M, Met; N, Asn; P, Pro; Q, Gln; P, Ar g; S, Ser; T, Thr; V, Val; W, Trp; and Y, Tyr. The nucleotide sequence has been deposited in GenBank (accession number: Y11306)

Figure 2A:
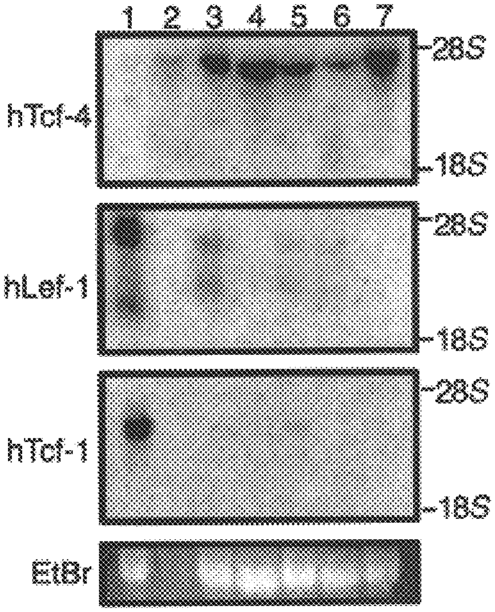
Figure 2B:
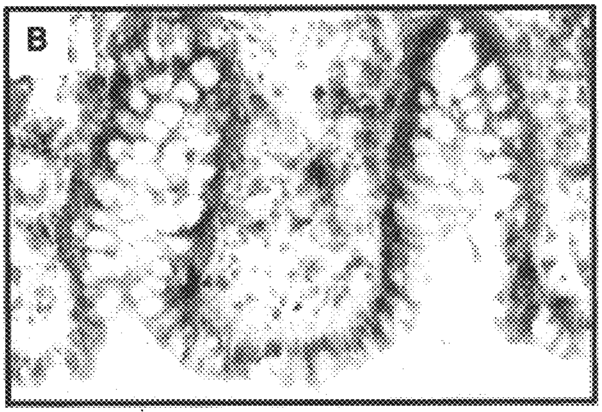
Figure 2C:
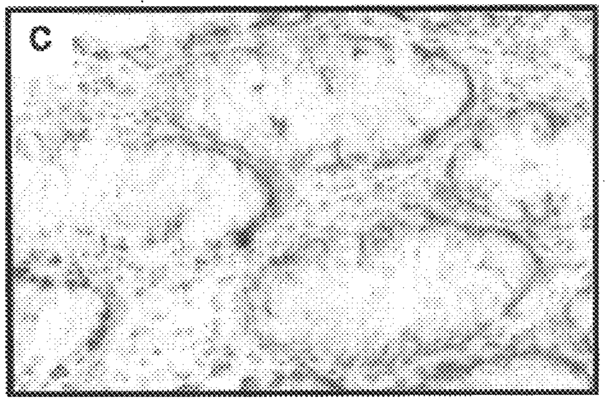

FIGS. 2A–2C. Analysis of hTcf-4 expression in colonic epithelium.

(FIG. 2A) Northern blot analysis of hTcf-4, hTcf-1, hLef-I expression in Jurkat T cells (lane 1); colonic mucosa (lane 2); colon carcinoma cell lines DLD-1 (lane 3), HCT116 (lane 4); SW480 (lane 5); SW620 (lane 6); HT29 (lane 7). Lane 2 contains 5 μg total RNA; all others contain 15 μg total RNA. The positions of 18S and 28S ribosomal RNAs are shown. EtBr, ethidium bromide stain. (FIG. 2B) In situ hybridization of healthy human colon tissue to an hTcf-4 probe. (FIG. 2C) In situ hybridization to a negative control probe (a fragment of the *E. coli* neomycin resistance gene).

Figure 3A:
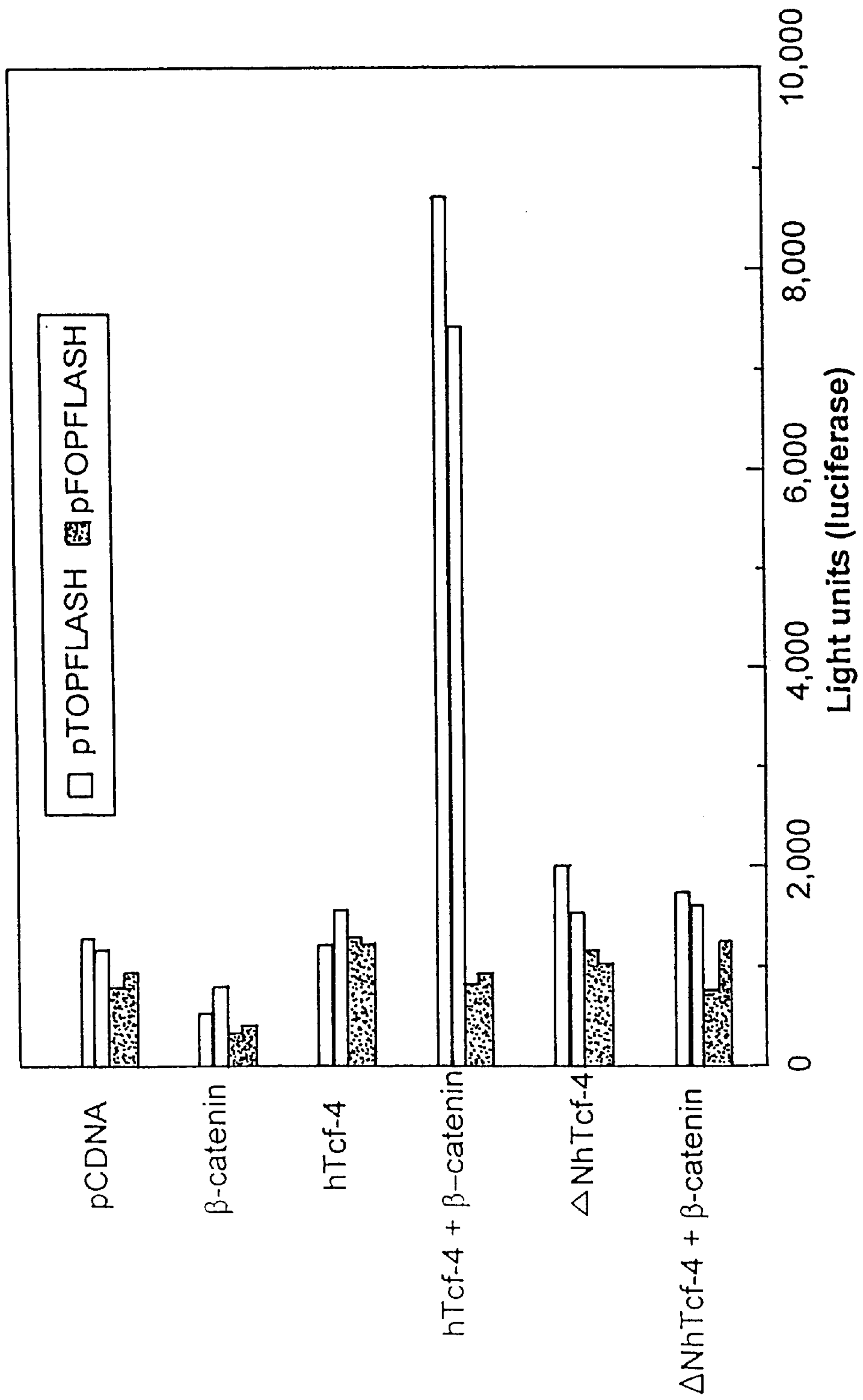
Figure 3C:
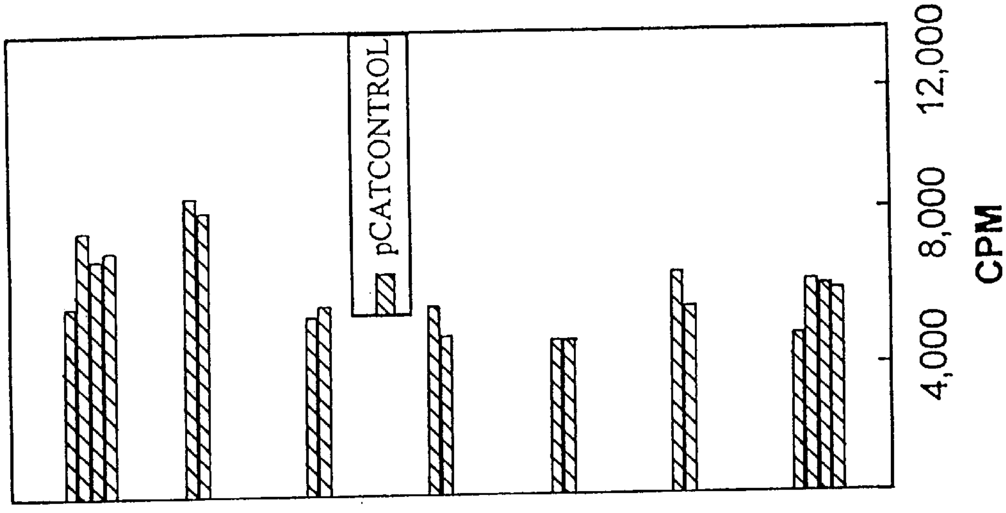
Figure 3B:
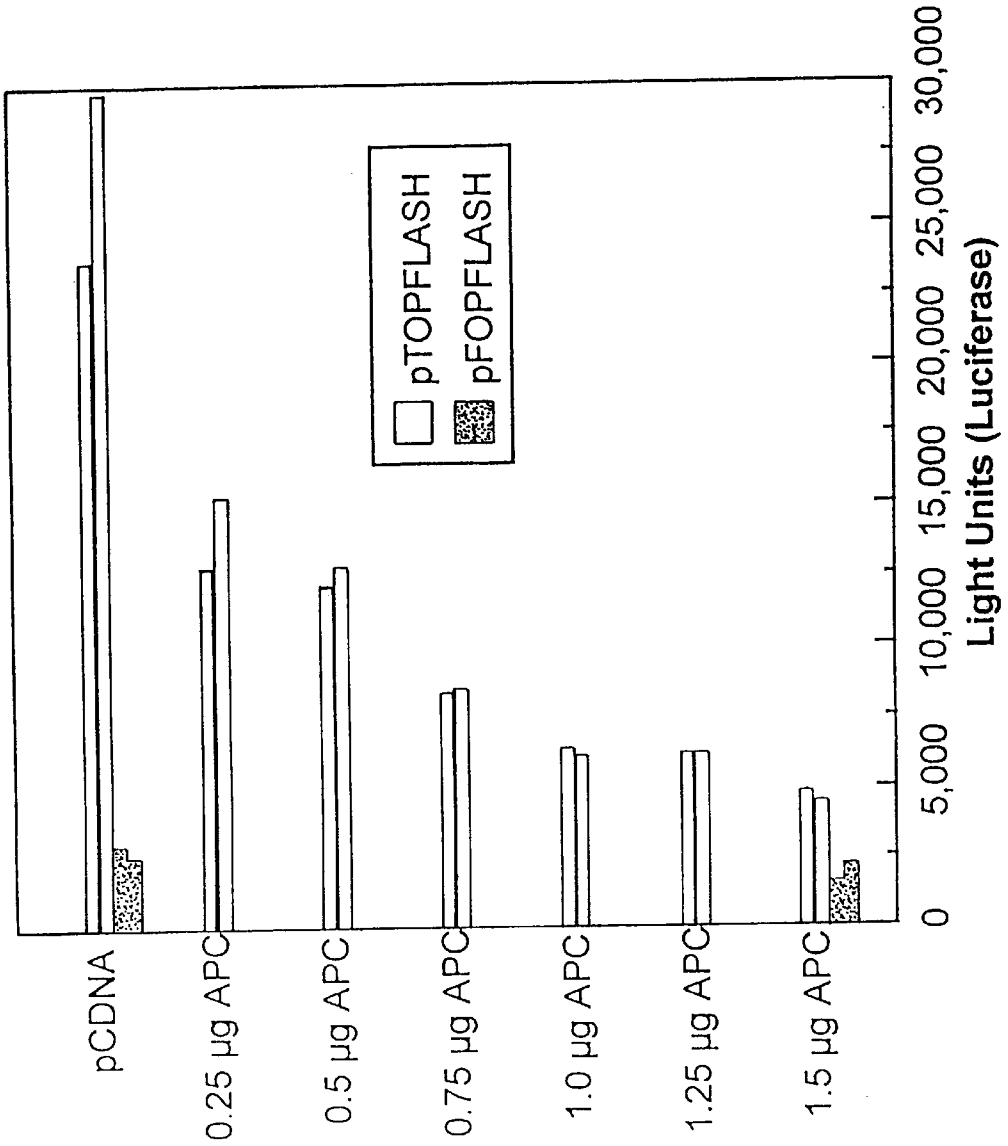

FIGS. 3A–3B. Transactivational properties of β-catenin/hTcf-4.

All reporter assays were performed as duplicate transfections. For each condition, both values are shown. (FIG. 3A) Reporter gene assays in IIA1.6 B cells. Cells were transfected by electroporation with 1 μg luciferase reporter plasmid, 5 μg β-catenin expression plasmid, and 3 II-hTcf-4 expression plasmids. Empty pCDNA was added to a total of 10 μg, plasmid DNA. (FIG. 3B) Reporter gene assays in SW480 colon carcinoma cells. Cells were transfected with 0.3 μg, of the indicated luciferase reporter gene, 0.7 μg pCATCONTROL as internal control, the indicated amounts of pCMVNeoAPC, and empty PCDNA to a total of 2.5 μg plasmid DNA. Control CAT values are given in the right panel.

Figure 4:
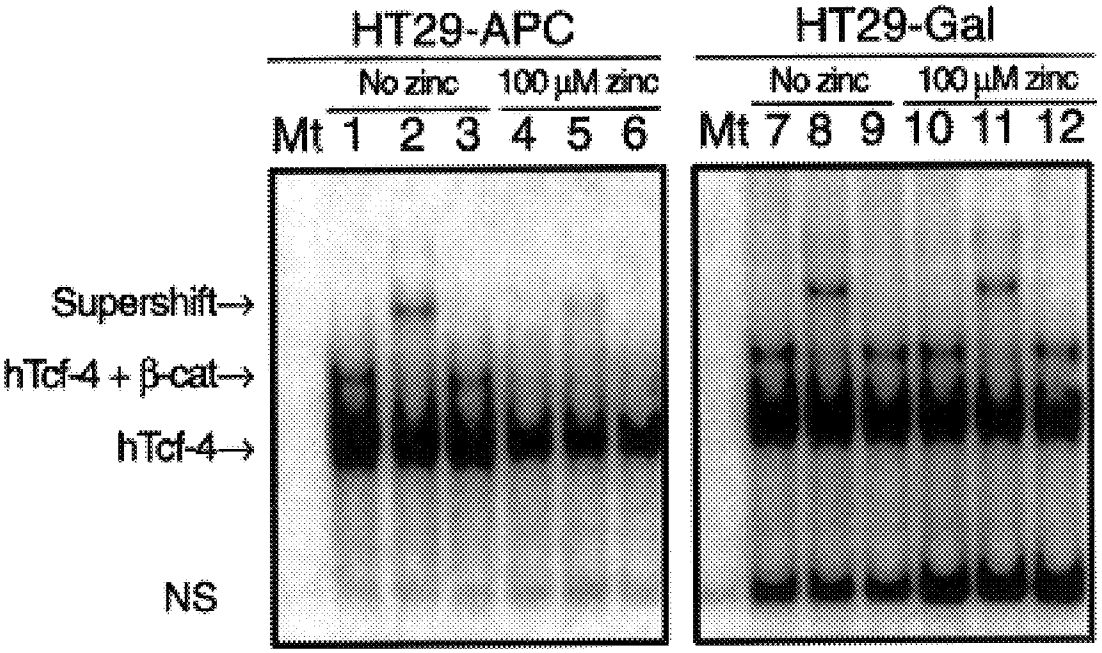

FIG. 4. Constitutive presence of β-catenin-hTcf-4 complexes in $APC^{-/-}$ cells. Gel retardation assays were performed on nuclear extracts from the indicated cell lines before and after a 20-hour exposure to $Zn^{++}$. Samples in lanes 1, 4, 7, 10 were incubated under standard conditions. To the samples in lanes 2, 5, 8, 11, 0.25 μg, anti β-catenin was added. To the samples in lanes 3, 6, 9, 12, 0.25 μg of a control (human CD4) antibody was added. N.S., nonspecific band also observed with mutant (nonbinding) probe (lane Mt).

Figure 5A:
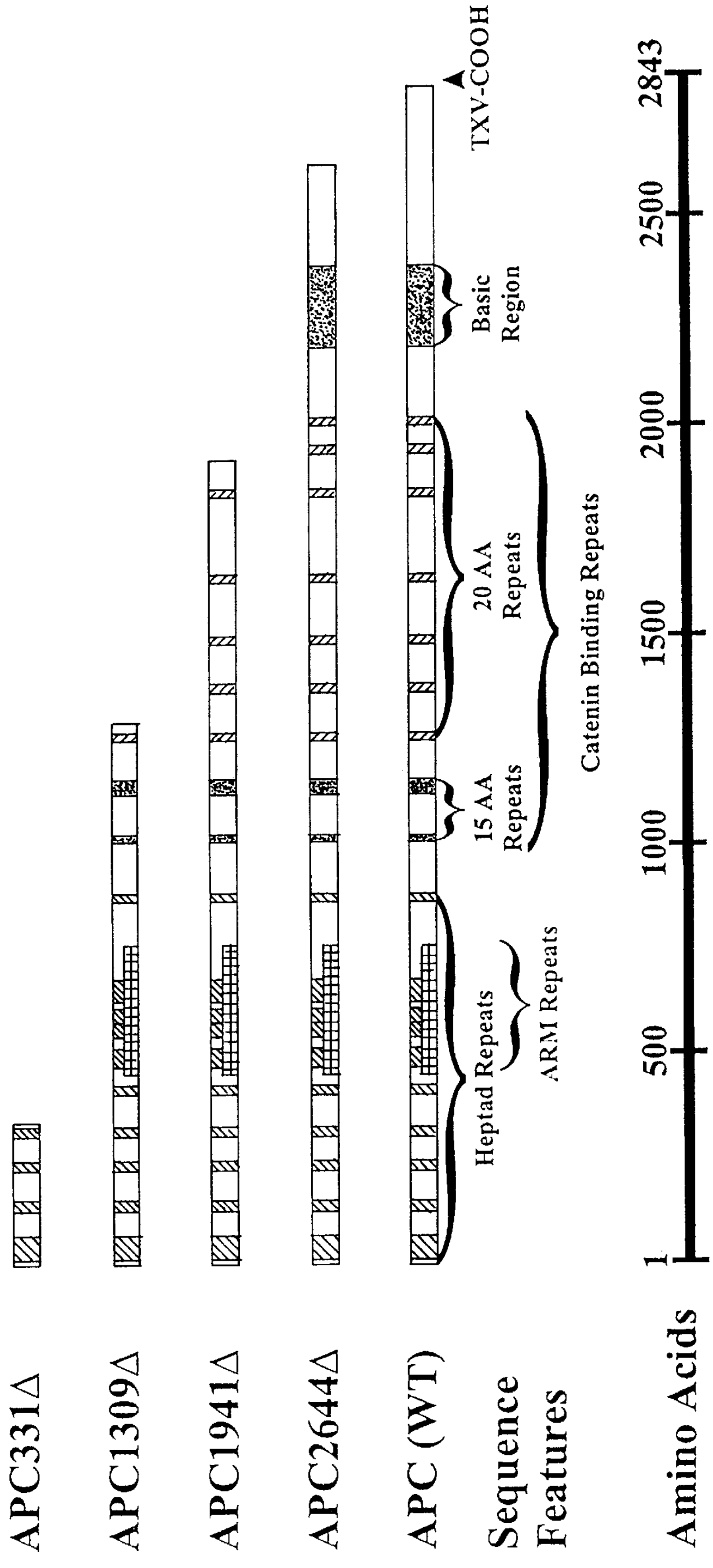
Figure 5B:
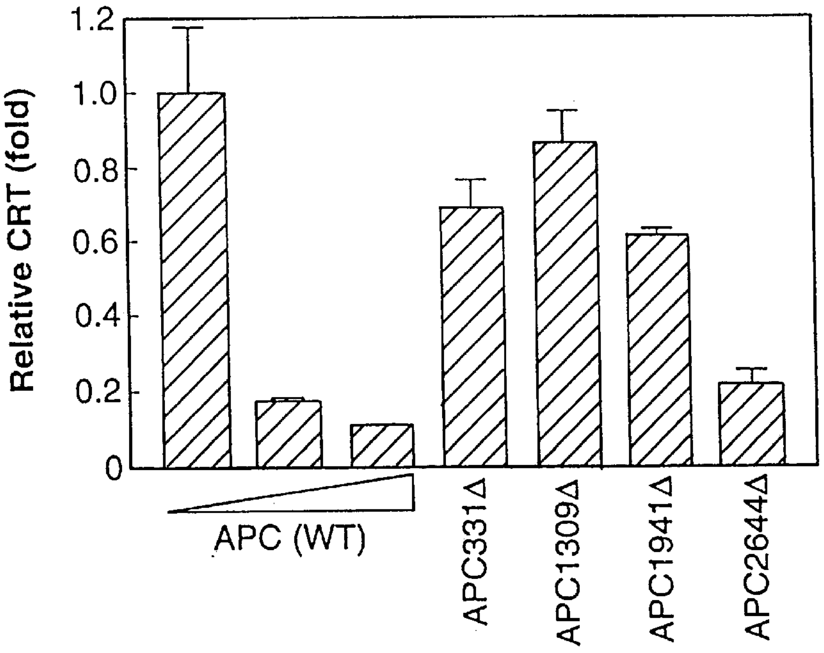

FIGS. 5A–5B. Effects of APC mutations on CRT. (FIG. 5A) Schematics of wild-type (WT) and mutant APC. APC is a 2843-amino-acid (AA) protein (32) with contains armadillo (ARM) repeats in the amino-terminus (33), 15 and 20 AA β-catenin-binding repeats in the central region (18,19), and a basic region in the carboxyl-terminus (32). The carboxyl-terminus also contains a TXV sequence which mediates DLG binding (22). (FIG. 5B) Effects of WT and mutant APC on CRT. SW480 cells containing endogenous mutant APC were transfected with the APC expression vectors shown in (FIG. 5A) and CRT was measured. Cells were transfected with increasing amounts of WT APC (0, 0.15 and 0.5 μg) or 0.5 μg mutant APC. CRT reporter activities are expressed relative to assays containing no WT APC and are the means of three replicates. Error bars represent standard deviations.

Lipofectamine was used to cotransfect SW480 cells with at internal control (0.5 μg pCMV-βgal), a reporter construct (0.5 μg pTOPFLASH or pFOPFLASH) and the indicated amount of the various APC expression vectors. The pTOPFLASH reporter contained an optimized Tcf-binding site 5' of a luciferase reporter gene, whereas pFOPFLASH contained a mutated site that does not bind Tcf The amount of DNA in each transfection was kept constant by addition of an appropriate amount of empty expression vector (pCEP4). Luciferase and β-galactosidase activities were determined 16 hours after transfection. Luciferase activity was corrected for transfection efficiency (using the control β-galactosidase activity) and nonspecific transcription (using the pFOPFLASH control).

Figure 6B:
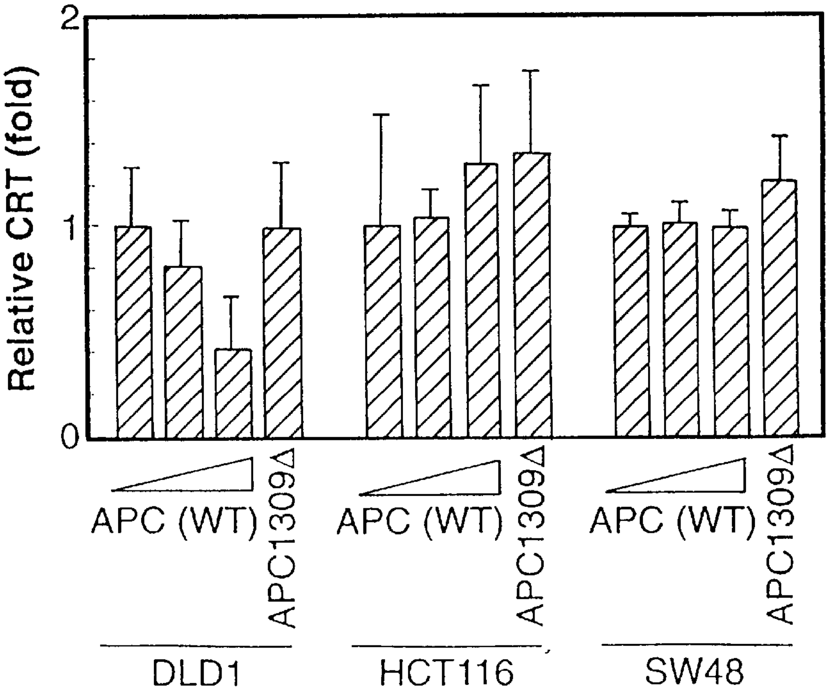
Figure 6A:
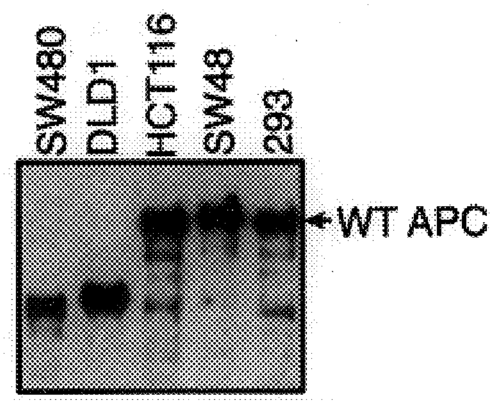

FIGS. 6A–6B. Evaluation of CRT in colorectal cancer cell lines with WT APC. (FIG. 6A) Immunoblot of endogenous APC in the DLD1, SW480, HCT116, SW48 and 293 cell lines, developed with APC monoclonal antibody FE9 (34). (FIG. 6B) Effects of exogenous WT APC on CRT in cell lines with endogenous mutated or WT APC. Cells were transfected with increasing amounts (0, 0.15 μg, 0.5 μg for DLD1 and SW48; 0, 0.5 μg, 5 μg for HCT116) of WT APC or APC1309Δ mutant (0.5 μg for DLD1 and SW48; 5 μg for HCT116) and CRT was assessed as in FIG. 5. CRT reporter activities are expressed relative to activity in extracts without exogenous APC and are the means of three replicates. Error bars represent standard deviations.

Figure 7A:
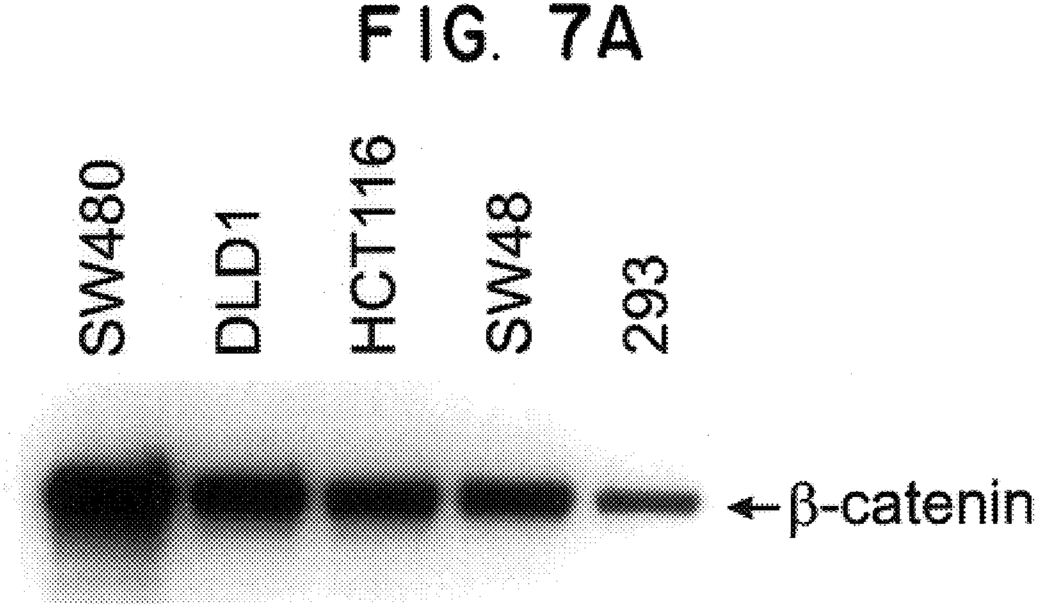
Figure 7B:
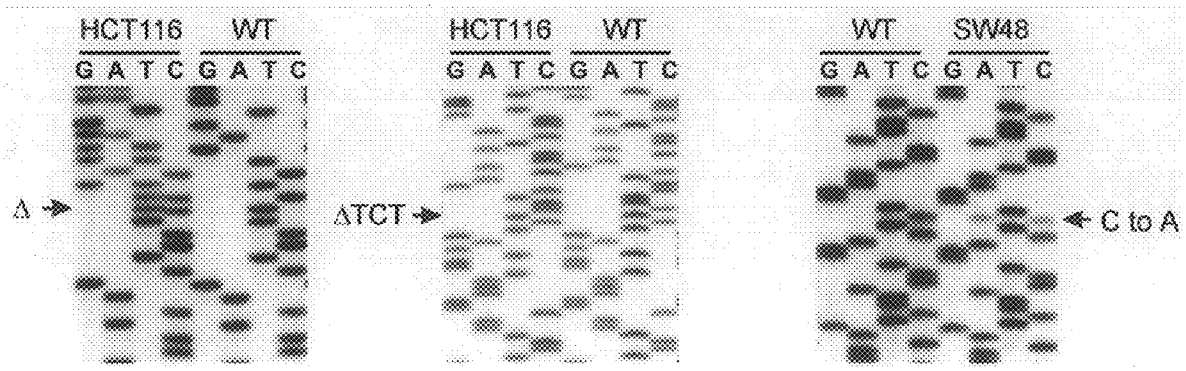
Figure 7C:
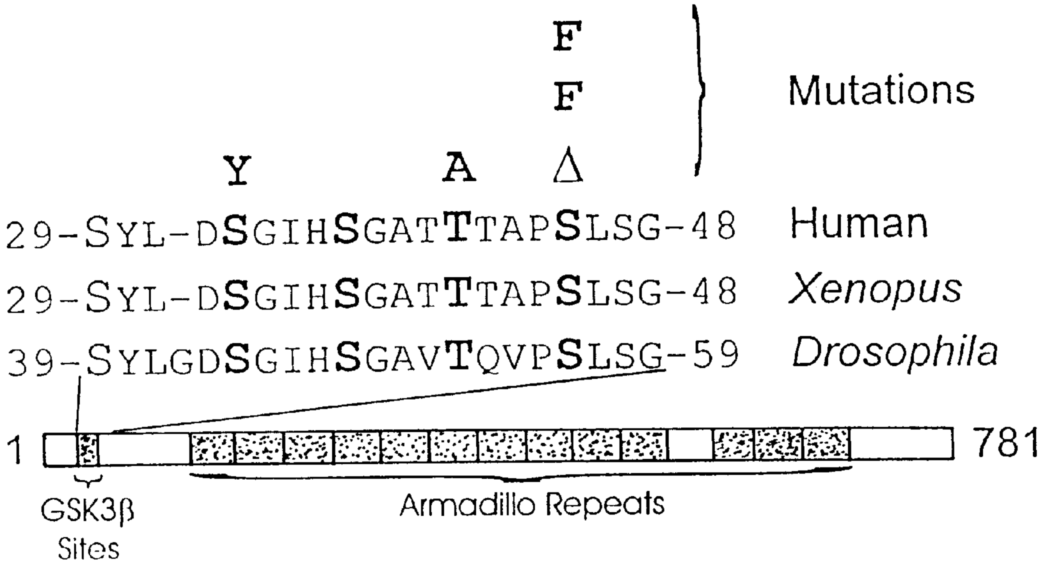

FIGS. 7A–7C. Evaluation of β-catenin in colorectal cancer cell lines with WT APC. (FIG. 7A) Immunoblot of the cell lines used in this study, developed with β-catenin monoclonal C19220 (Transduction Laboratories, Lexington, Ky.)(31). (FIG. 7B) Sequence of CTNNB1 in HCT116 and SW48. Overlapping segments constituting the entire CTNNB1 were amplified by RT-PCR from SW480, DLD1, HCT116, and SW48 cells, and sequenced directly with ThermoSequenase (Amersham). In the case of HCT116, a PCR product containing the deleted region was also cloned into pCI-neo (Promega, Madison) and multiple clones corresponding to each allele were individually sequenced.

The left panel (nts 121 to 143 from HCT116) reveals the presence of a deletion in addition to the WT sequence. The middle panel (antisense strand 156 to 113 of the WT and deleted alleles of HCT116) reveals the 3-bp deletion (ΔTCT) that removed codon 45 in half the clones. The right panel (nts 80 to 113 from SW48) reveals a C to A transition affecting codon 33 (TCT -to TAT). (FIG. 7C) Schematic of β-catenin illustrating the armadillo repeats (33) and negative regulatory domain (Human and Xenopus, SEQ ID NO: 10; Drosophila, SEQ ID NO: 11). The residues in larger type fit the consensus sequence for GSK3β phosphorylation (29) and those in bold have been demonstrated to affect down regulation of β-catenin through GSK3β phosphorylation in Xenopus embryos (27). The five mutations found in human colon cancers are indicated at the top.

Figure 8A:
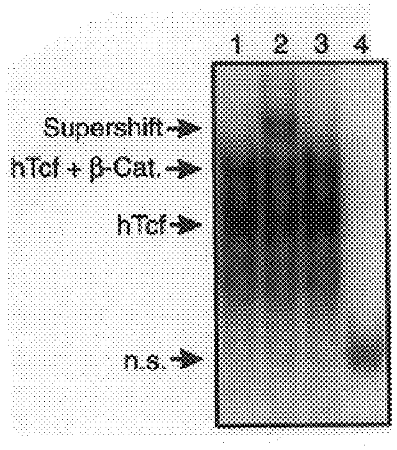
Figure 8B:
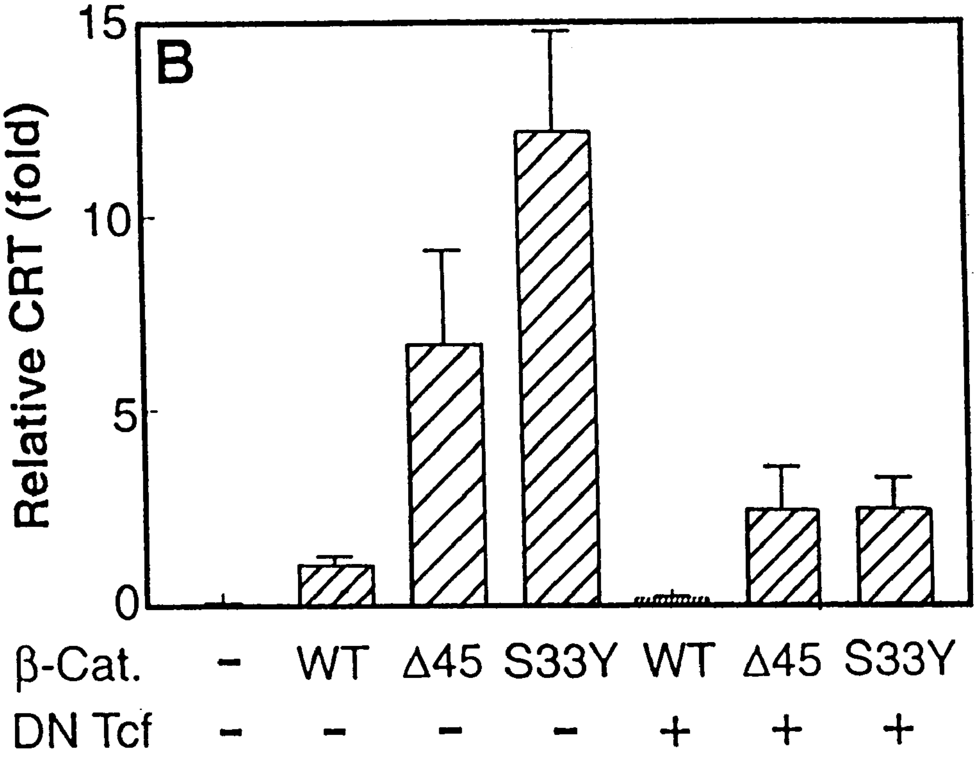

FIGS. 8A–8B. Functional evaluation of β-catenin mutants. (FIG. 8A) Constitutive nuclear complex of β-catenin and Tcf in HCT116 cells. The presence of nuclear -β-catenin-Tcf complexes was assessed by gel shift assays. Lanes 1 to 3, optimal Tcf retardation probe shifted with nuclear extract from HCT116 cells with addition of no antibody (lane 1), anti β-catenin (0.25 μg, lane 2), or an irrelevant antibody (0.25 μg, lane 3). Lane 4, mutant Tcf retardation probe shifted with nuclear extract from HCT116 cells. n.s., nonspecific shifting seen with the mutant probe. (FIG. 8B) Effects of the β-catenin mutations on CRT. 293 cells were transfected with WT (WT) or mutant (A45, S33Y) β-catenin and CRT was assessed. CRT reporter activities are expressed relative to WT β-catenin and are the means of three replicates. Error bars represent standard deviations. β-catenin expression constructs were prepared as follows. WT CTNNB1 was amplified by, RT-PCR from SW480 cells and cloned into the mammalian expression vector pCI-neo (Promega) to produce pCI-neo-β-cat. The pCI-neo-β-cat Δ45 and S33Y were generated by replacing codons 1 to 89 in. pCI-neo-β-cat with a PCR product encoding the equivalent region from HCT116 or SW48 cDNA, respectively. The structures of all constructs were verified by sequence analysis. Lipofectamine was used to cotransfect 293 cells with an internal control (0.1 μg CMV-βgal), a reporter (0.5 μg pTOPFLASH or pFOPFLASH), a Tcf-4 expression vector (0.5 μg pCDNA-TCF4), and β-catenin (0.5 μg) or dominant negative hTcf-4 1.0 μg) expression vectors. CRT was determined as described above.

DETAILED DESCRIPTION

It is a discovery of the present invention that hTcf-4 binds to β-catenin and activates transcription in colorectal epithelial cells. Moreover, it has now been found that APC regulates this transcriptional activation, at least in part by binding to β-catenin. In colorectal cancer cells this regulation is frequently abrogated, either by mutation of APC or by mutation of β-catenin.

Two alternative splice forms of human Tcf-4 have been found. One form (hTcf-4E) is homologous to hTcf-1E and the other (hTcf-4B) is homologous to hTcf-1B. The sequence of the nucleotide and amino acid sequences are shown in SEQ ID NOs: 1, 2, 5, and 6. The coding sequences and proteins can be used in assays as described below. Intron-free DNA molecules are provided which are originally made by reverse transcription of a mRNA molecule. They can be propagated in cells or amplified as is desired. Isolated Tcf-4 proteins can be provided substantially free of other human proteins if, for example, the nucleotide sequences are expressed in non-human cells. Methods and vectors for achieving such expression are well known in the art. Choice of such expression means is made by the skilled artisan according to the desired usage and convenience.

Cells can be tested to determine if they have a wild-type APC or a wild-type downstream protein in the APC transcription regulatory pathway, called herein the CRT pathway (β-catenin/Tcf-regulated transcription). One protein within the CRT pathway which has been identified as a target of mutations in human cancers is β-catenin (encoded by the CTNNB1 gene). Other parts of the pathway are also likely to be targets. Although the target genes of the CRT pathway have not been identified, they can be readily identified using the system disclosed here. Genes which are differentially transcribed in the presence of wild-type and mutant CTNNB1, for example, can be identified.

Tcf-responsive reporter genes are those constructs which comprise a readily detectable or assayable gene (such as luciferase, β-galactosidase, chloramphenicol acetyltransferase) linked in cis to a Tcf-responsive element. Such responsive elements are known in the art (7) and any such elements can be used. An optimal Tcf motif contains the sequence CCTTTGATC. From one to twenty copies, and preferably from three to six copies, of the motif may be used. Mutation of the sequence to CCTTTGGCC abrogates responsiveness. Another necessary part of such constructs is a minimal promoter, such as the c-Fos or the Herpes virus thymidine kinase promoter. Transcription of the reporter gene may be performed by any means known in the art, usually by assaying for the activity of the encoded gene, although immunological detection methods can also be used. In addition, transcription can be monitored by measuring the transcribed mRNA directly, typically using oligonucleotide probes.

As shown below, a cell which has a wild-type APC protein will inhibit CRT. However, most mutations in APC render APC unable to inhibit CRT. Similarly, certain mutations in CTNN1 render β-catenin super-active and/or refractory to the inhibition by APC. Thus measuring Tcf-responsive reporter gene transcription is an indication of the status of APC and CTNNB1. Mutations in both of these genes are associated with cancers and therefore provides diagnostic and prognostic information.

Assays for CRT can be accomplished in vitro or in cells. If the assay is to be accomplished in cells, then a Tcf-responsive reporter gene must be introduced into the cell. Any means for introducing genetic material into cells can be used, including but not limited to infection, transfection, electroporation. If the assay is to be performed in vitro then the components for transcription must be present. These include suitable buffers, RNA polymerase, as well as ribonucleotides. If the protein product is to be assayed, then the components for translation must also be present, such as ribosomes, and amino acids.

These assays can also be used to screen compounds for potential as anti-cancer therapeutic agents. Using either the in vitro or cell form of the assay, test compounds can be introduced to determine whether they are able to mimic the effect of wild-type APC or to convert a mutant APC into a form which is able to inhibit CRT or a mutant β-catenin into a form which is regulatable by APC. In addition, compounds can be tested for the ability to inhibit the binding of β-catenin and Tcf-4, thus mimicking the action of APC. Such a test can be conducted in vitro or in vivo, for example using a two hybrid assay.

A means for diagnosis of cancers is the result of the observation that CTNNB1 mutations are found in tumor cells, especially those which have wild-type APC. Such mutations can be found, inter alia, by sequencing either the gene or the protein found in a sample. Functional assays can also be used, such as whether β-catenin binds to APC or Tcf-4, or whether it is capable of mediating CRT. Sequences can be compared to those found in a normal tissue of a human, especially the same human who provided the sample being tested. Suitable tumors for testing include, but are not limited to those which are associated with FAP. Suitable tumors include colorectal cancer, thyroid cancer, brain cancer, medulloblastoma, desmoid tumor, osteoma, breast cancer, and head and neck cancer. Because APC mutations are so frequent, and because it appears that APC mutations do not occur in the same tumors as CTNNB1 mutations, one can prescreen samples for APC mutations before performing a CTNNB1 determination.

The portion of the APC gene which encodes the β-catenin binding site can be used in a gene therapy format. Suitable techniques are known in the art for administering genes to tumors, and any such technique can be used. Suitable expression vectors are also known in the art and it is within the skill of the artisan to select an appropriate one. Upon expression in a tumor cell of the β-catenin binding portion of APC, β-catenin will be bound and titrated away from binding to Tcf-4, thus preventing unregulated expression of the CRT target genes. Similarly, a polypeptide portion of APC containing the β-catenin binding site can be administered to cells to perform a titration of β-catenin. Techniques for such administration to cells is well known in the art. Cells which are treated with either the polynucleotide or the polypeptide can be used to study the interaction between APC and β-catenin, and for developing drugs which interfere with such binding.

The above disclosure generally describes the present invention. A more complete understanding can be obtained by reference to the following specific examples which are provided herein for purposes of illustration only, and are not intended to limit the scope of the invention.

EXAMPLE 1

This example identifies Tcf-4 as the expressed family member in colorectal epithelial cells and provides the complete sequence of the cloned cDNA.

There are four known members of the Tcf/Lef family in mammals: the lymphoid-specific factors Tcf- I and Lef- 1 (7,8), and the less well characterized Tcf-3 and 4(9). We performed a qualitative Reverse Transcriptase-Polymerase Chain. Reaction assay for expression of the four Tcf/Lef genes on 43 colon tumor cell lines. While most colon cell lines expressed more than one of the genes, only hTcf-4 mRNA was expressed in essentially all lines.

We then screened a human fetal cDNA library and retrieved clones encoding full-length hTcf-4 (FIG. 1). A genomic fragment encoding, the HMG box region of hTcf-4 (7) was used to probe a human 12 week-fetal cDNA library in Lambda GT-11. Positive clones were subcloned into pBluescriptSK and sequenced. See SEQ ID NOs: 1 and 2. The predicted sequence of hTcf-4 was most similar to that of hTcf-1. Alternative splicing yielded two COOH-termini that were conserved between hTcf- I and hTcf-4. The $NH_2$-terminus, which in hTcf- 1, mLef-1 and Xenopus TCF-3 mediates binding to β-catenin (6), was also conserved in hTcf-4. Northern blot analysis of selected colon carcinoma cell lines revealed high-level expression of hTcf-4 (FIG. 2A). Northern blot hybridizations (7) were performed with full-length hTfc-1, hLef-I and hTcf-4 cDNA. Colon epithelial cells were freshly prepared from a mucosal preparation dissected from a healthy surgical colon sample. The sample was minced, and incubated with 1 mM dithiothreitol (DTT) in Hanks' medium to remove mucus. Single-cell suspensions were prepared by incubation at RT in 0.75 mM EDTA in Hanks' medium. Epithelial cells were separated from lymphocytes by Percoll gradient centrifugation.

As evidenced by in situ hybridization (FIG. 2, B and C) and Northern blotting (FIG. 2A), hTcf-4 MRNA was readily detectable in normal colonic epithelium, whereas hTc-I and hLef-I were not detectable. In situ hybridization of 6 μ frozen sections of healthy colon biopsy samples were performed as described(10). hTcf-4 cDNA encoding amino acids 200 to 310 was amplified and labeled with Dig-11-dUTP (Boehringer Mannheim, Germany) by PCR. After hybridization and washing, the sections were sequentially incubated with mouse anti-Dig antibody (Boehringer) and a horseradish peroxidase conjugated rabbit antibody to mouse immunoglobulin (Dako, Glostrup, Denmark). The signal was visualized with diaminobenzidine, which produces a reddish-brown precipitate. Blue counterstining was performed with haematoxyline.

EXAMPLE 2

This example demonstrates the interaction of Tcf-4 and β-catenin and their function as a transcriptional activating factor.

To investigate whether hTcf-4 functionally interacts with β-catenin, we used two sets of reporter constructs in a β-catenin-Tcf reporter gene assay (7). One contained three copies of the optimal Tcf motif CCTTTGATC, or three copies of the mutant motif CCTTTTGGCC, upstream of a minimal c-Fos promoter driven-luciferase expression (PTOPFLASH and PFOPFLASH). The second set contained three copies of the optimal motif, or three copies of the mutant motif, upstream of a minimal Herpes virus thymidine kinase promoter driven-Chloramphenicol Acetyl Transferase (CAT) expression (PTOPCAT and PFOPCAT, respectively). Reporter gene assays were performed as in (7). In brief, $2 \times 10^6$ cells were transfected with plasmids by electroporation. After 24 hours, cells were harvested and lysed in 1 mM DTT, 1% Triton X-100, 15% glycerol, 25 mM Tris pH 7.8 and 8 mM $MgCl_2$. cDNAs encoding Myc-tagged versions of β-catenin and hTcf-4 were inserted into the mammalian expression vector pCDNA (Invitrogen). PCATCONIROL, encoding the CAT enzyme under the control of the SV40 promoter, was purchased from Promega.

Epitope-tagged hTcf-4 and a deletion mutant lacking, the $NH_2$-terminal 30 amino acids (ΔNhTcf-4) were cloned into the expression vector pCDNA. Transient transfections were performed in a murine B cell line (IIA1.6), that does not express any of the Tcf genes (6).

The TOPFLASH reporter was strongly transcribed upon cotransfection with the combination of β-catenin and hTcf-4 plasmids, but not with the individual plasmids or with the combination of β-catenin and ΔNhTcf-4 plasmids. No enhanced transcription was detected in cells transfected with the negative control PFOPFLASH (FIG. 3A). These results show that interaction of the $NH_2$-terminus of hTcf-4 with β-catenin results in transcriptional activation.

EXAMPLE 3

This example demonstrates the functional regulation of CRT transcriptional activation by wild-type APC.

In three $APC^{-/-}$ carcinoma cell lines, SW480, SW620 and DLD-1 (FIG. 3B), the PTOPFLASH reporter was 5–20 fold more actively transcribed than PFOPFLASH. Importantly, transfection of SW480 cells with the reporter gene and an APC-expression vector abrogated the transcriptional activity in a dose-dependent manner (FIG. 3B). In contrast APC had no effect on a cotransfected internal control (pCATCONTROL), or on the basal transcription of PFOP-FLASH (FIG. 3B). The use of PTOPCAT and PFOPCAT instead of PTOPFLASH and PFOPFLASH led to comparable observations. The constitutive transcriptional activity of Tcf reporter genes in $APC^{-/-}$ colon carcinoma cells was in stark contrast to the inactivity of these genes in non-colonic cell lines, including IIA1.6 B cells (FIG. 3A), the C57MG breast carcinoma cell line; the Jurkat and BW5147 T cell lines; the Daudi and NS1 B cell lines; the K562 erythromyeloid cell line; the HeLa cervical carcinoma line; the HepG2 hepatoma cell line; 3T3, 3T6, and Rat-I fibroblasts; and the kidney derived SV40-transformed COS cell line (7,16).

EXAMPLE 4

This example demonstrates that a functional β-catenin-hTcf-4 complex exists constitutively in $APC^{-/-}$ cells.

We used HT29-$APC^{-/-}$ colon carcinoma cells (12), in which APC is controlled by a metallothionein promoter. Induction by $Zn^{++}$restores wild-type levels of APC, and leads to apoptosis (12). HT29-Gal cells which carry a $Zn^{++}$-inducible LacZ gene were used as a control. The only Tcf family member expressed in HT29 is hTcf-4 (FIG. 2C). In nuclear extracts from uninduced HT29 derived transfectants, we readily detected hTcf-4 by gel retardation (FIG. 4). An additional band of slightly slower mobility was also observed. The addition of a β-catenin antibody resulted in the specific retardation of the latter band, indicating that it represented a β-catenin-hTcf-4 complex (FIG. 4) (12). After $Zn^{++}$ induction for 20 hours, the β-catenin-hTcf-4 complex was diminished sixfold relative to uncomplexed hTcf-4 in HT29-APC1, while no significant change was observed in HT29-Gal cells (FIG. 4). Importantly, the overall levels of cellular β-catenin do not change during the induction period in HT29-APC1 cells (12).

Gel retardation assays were performed as described elsewhere (7). Extracts were prepared from intact nuclei that were washed four times to avoid contamination with cytoplasmic β-catenin. As the optimal Tcf/Lef probe, we used a double-stranded 15-mer CCCTTTGATCTTACC (SEQ ID NO:3); the control probe was CCCTTTGGCCTTACC (SEQ ID NO:4). (All oligonucleotides were from Isogene, Holland). The β-catenin antibody was purchased from Transduction Laboratories (Lexington, Ky.). A typical binding reaction contained 3 μg nuclear protein, 0.1 ng radiolabeled probe, 100 ng of dIdC, in 25 μl of binding buffer (60 mm KCl, 1 mM EDTA, 1 mM DTT, 10% glycerol). Samples were incubated for 20 min at room temperature, antibody was added, and the samples incubated 20 min further.

On the basis of these data, we propose the following model. In normal colonic epithelium hTcf-4 is the only expressed member of the Tcf family. The interaction of β-catenin with hTcf-4 is regulated by APC. When appropriate extracellular signals are delivered to an epithelial cell, β-catenin accumulates in a form that is not complexed with GSK3β-APC, and that enables its nuclear transport and association with hTcf-4. The HMG domain of hTcf-4 binds in a sequence-specific fashion to the regulatory sequences of specific target genes; β-catenin supplies a transactivation domain. Thus, transcriptional activation of target genes occurs only when hTcf-4 is associated with β-catenin. The hTcf-4 target genes remain to be identified. However, the link with APC and catenin suggests that these genes may participate in the generation and turnover of epithelial cells. Upon loss of wild-type APC, monomeric β-catenin accumulates in the absence of extracellular stimuli, leading to uncontrolled transcription of the hTcf-4 target genes. The apparent de novo expression of other members of the Tcf family in some colon carcinoma cell lines might lead to a further deregulation of Tcf target gene expression by the same mechanism. The control of β-catenin -Tcf signaling is likely to be an important part of the gatekeeper function of APC (19), and its disruption an early step in malignant transformation.

EXAMPLE 5

This example demonstrates that mutant APC protein does not regulate CRT and that a complete set of 20-AA repeats in APC is required to mediate inhibition of CRT.

We tested four APC mutants (FIG. 5A) for their ability to inhibit β-catenin/Tcf-regulated transcription (CRT) in transfection assays. The first mutant, APC331Δ represents a type of mutation found in the germline of Familial Adenomatous Polyposis (FAP) patients as well as in sporadic tumors (15). The APC331Δ protein is truncated at codon 331, amino-terminal to the three 15-amino-acid (AA) β-catenin-binding repeats between codons 1020 and 1169. The second mutant, APC1309Δ, is the most common germline APC mutation (15), a 5-bp deletion that produces a frameshift at codon 1309 and truncation of the protein. The APC1309Δ protein retains the 15-AA β-catenin repeats but lacks the seven 20-AA repeats between codons 1323 and 2075 that have been implicated in binding and phosphorylation of β-catenin (18). The third mutant, APC1941Δ, represents one of the most distal somatic mutations observed in colorectal tumors (25). The APC1941Δ protein is truncated at codon 1941 and therefore contains the 15-AA repeats and all but the last two 20-AA repeats. Finally, APC2644Δ represents a germline mutation resulting from a 4-bp deletion in codon 2644. Patients with this type of unusual carboxyl-terminal mutation develop few polyps (attenuated polyposis) but have pronounced extracolonic disease, particularly desmoid tumors (26).

Each of the APC mutants was cotransfected with a CRT reporter into the SW480 colorectal cancer cell line. SW480 cells have truncated APC and constitutively active CRT which can be suppressed by exogenous WT APC. Although all four mutants produced comparable levels of APC protein after transfection, they varied in their CRT inhibitory activity. The three mutants found in patients with typical polyposis or cancer were markedly deficient in inhibition of CRT (FIG. 5B). The reduced activity of APC1309Δ and APC1941Δ suggests that β-catenin binding is not sufficient for APC-mediated inhibition of CRT and that the complete set of 20-AA repeats is required. Interestingly, the inhibitory activity of the APC2644Δ mutant associated with attenuated polyposis was comparable to that of WT APC (FIG. 5B), suggesting that the DLG-binding domain at the carboxyl-terminus of APC is not required for down-regulation of CRT.

WT and mutant APC constructs (2 μg) were transfected into 293, SW480, and HCT116 cells using Lipofectamine (GIBCO/BRL, Gaithersburg). Protein was harvested 24 hours later and subjected to immunoblot analysis with APC monoclonal antibody FE9 (23). In HCT116 and 293 cells, exogenous WT APC comigrated with the endogenous APC. In SW480 cells, APC1309Δ comigrated with the endogenous mutant APC. In all other cases, the nonfunctional APC constructs (APC331Δ, APC 1309Δ, and APC1941Δ) produced as much or more protein than the CRT-functional forms of APC (APC WT and APC 2644Δ).

EXAMPLE 6

This example demonstrates that other components of the APC-regulatory pathway are affected in some cancer cells.

We evaluated CRT in two colorectal tumor cell lines (HCT116 and SW48) that express full-length APC (FIG.

6A). Both HCT116 and SW48 displayed constitutively active CRT and, in contrast to cell lines with truncated APC (DLD1 and SW480), this activity was not inhibited by exogenous WT APC (FIG. 5B, 6B). Other (noncolorectal cancer) cell lines expressing WT APC do not display constitutive CRT activity. These transfection results suggested that the constitutive CRT in HCT116 and SW48 might be due to an altered downstream component of the APC tumor suppressor pathway.

EXAMPLE 7

This example demonstrates a defect in the gene encoding β-catenin in some cancer cells, which affects CRT.

We evaluated the status of a likely candidate for a downstream component of the APC tumor suppressor pathway, β-catenin, in the same four lines. All four lines expressed similar amounts of apparently intact β-catenin, as assessed by immunoblots (FIG. 7A). However, sequence analysis revealed that both HCT116 and SW48 harbored mutations in the β-catenin gene (CTNNB1) (FIG. 7B). HCT116 had a 3-bp deletion that removed one AA (Ser-45), and SW48 had a C to A missense mutation that changed Ser-33 to Tyr. Analysis of paraffin-embedded archival tissue from the HCT116 patient confirmed the somatic nature of this mutation and its presence in the primary tumor prior to culture. Interestingly, both mutations affected serines that have been implicated in the downregulation of β-catenin through phosphorylation by the ZW3/GSK3β kinase in Xenopus embryos (FIG. 7C) (27,28).

Genomic DNA was isolated from paraffin-embedded normal and tumor tissue from the patient from whom the HCT116 cell line was derived. A 95 bp PCR product encompassing the mutation was then amplified by PCR and directly sequenced using THERMOSEQUENASE (Amersham). The 3 bp deletion was observed in tumor but not in normal tissue.

To test the generality of this mutational mechanism, we evaluated five primary colorectal cancers in which sequencing of the entire coding region of APC revealed no mutations (25). Three of these five tumors were found to contain CTNNB1 mutations (S45F, S45F, and T44A) that altered potential ZW3/GSK3β phosphorylation sites (FIG. 7C). Each mutation appeared to affect only one of the two CTNNB1 alleles and to be somatic.

Genomic DNA was isolated from frozen-sectioned colorectal cancers and a 1001 bp PCR product containing exon 3 of CTNNB1 was then amplified by PCR and directly sequenced using ThermoSequenase (Amersham). An ACC to GCC change at codon 41 (T41A) and a TCT to TTT at codon 45 (S45F) was observed in one and two tumors, respectively.

EXAMPLE 8

This example demonstrates dominant mutations of CTNNB1 that render CRT insensitive to the effects of WT APC.

Because the β-catenin mutations were heterozygous, we hypothesized that the mutations might exert a dominant effect, rendering a fraction of cellular β-catenin insensitive to APC-mediated down regulation. To test this notion, we performed gel shift analyses with nuclear extracts from untransfected HCT116 cells. In contrast to noncolorectal cancer cell lines with intact APC, HCT116 cells contained a β-catenin/Tcf complex that gel-shifted an optimized Tcf-binding oligonucleotide, and this complex supershifted with anti-β-catenin (FIG. 8A). We also constructed β-catenin expression vectors and compared the biologic activity of the mutant β-catenin from HCT116 (β-Cat Δ45) and SW48 (β-Cat S33Y) with that of their WT counterpart. For these experiments, we used the 293 kidney epithelial cell line as it is highly transfectable, exhibits low endogenous CRT, and contains a high level of endogenous APC (FIG. 6A). In the presence of endogenous APC, both mutant β-catenins were at least 6-fold more active than the WT protein and this activity was inhibited by dominant-negative hTcf-4(FIG. 8B).

Together, these results indicate that disruption of APC-mediated regulation of CRT is critical for colorectal tumorigenesis. This is most commonly achieved by recessive inactivating mutations of both APC alleles but, as shown here, can also be achieved by dominant mutations of CTNNB1 that render CRT insensitive to the effects of WT APC. Our results suggest that APC inhibition of CRT requires phosphorylation of β-catenin at multiple sites. These potential phosphorylation sites are consistent with the known specificity of ZW3/GSK3β (29) a serine kinase that negatively regulates β-catenin in Xenopus and Drosophila cells (27) and that interacts with APC and β-catenin in mammalian cells (23). These results also suggest a functional basis for the occasional CTNNB1 mutations observed in other tumor types (30) and illustrate how a critical pathway in human disease can be illuminated by the discovery of mutations in different components of the pathway. The next step in understanding APC function will be the identification of the genes that are activated by hTcf-4/β-catenin complexes and inhibited by WT APC. These genes are likely to be related to APC's ability to induce apoptosis in colorectal cancer cells (31).

REFERENCES

1. B. Rubinfeld et al *Science,* 262, 1731 (1993); L. K. Su, B. Vogelstein, K. W. Kinzler, ibid 262, 1734 (1993).
2. B. Gumbiner, *Curr. Opin.* Cell Biol. 7; 634 (1995).
3. B. Rubinfeld et al, Science 272, 1023 (1996).
4. J. Papkoff, B. Rubinfeld, B. Schryver, P. Polakis, *Mol. Cell. Biol.* 16, 2128 (1996).
5. S. Munemitsa, B. Souza, I. Albert, B. Rubinfeld, P. Polakis, *Proc. Natl. Acad Sci. U.S.A.* 92, 3046 (1995); B. Rubinfeld, B. Souza, I. Albert, S. Muneinitsa, P. Polakis, *J Biol Chem.* 270, 5549 (1995).
6. M. Molenaar et al, *Cell* 86, 396 (1996); J. Behrens et al, *Nature* 382, 638 (1996); O. Huber et al., *Mech. Dev.* 59, 3 (1996).
7. M. van de Weterinc,, M. Oosterwegel, D. Dooijes, H. Clevers, EMBO J 10, 123 (1991); M. van de Weterig, J. Castrop, V. Korinek, *Mol Cell Biol,* 16, 745 (1996).
8. A. Travis et al. *Genes Dev.* 5, 880 (1991); M. L. Waterman, W. H. Fischer, K. A. Jones ibid. p. 6562. H. Clevers and R. Grosschedl, *Immunol. Today* 17, 336 (1996).
9. J. Castrop, K. van Norren, H. C. Clevers. *Nucleic Acids Res.* 20, 611 (1992).
10. E. van Hoffen et al, *Am. J Pathol* 149, 1991 (1996).
11. M. van de Wetering, M. Oosterwegel, K. van Norren, H. Clevers, EMBO J. 12, 3847 (1993)
12. P. Morin, B. Vogelstein, K. W. Kinzler, *Proc. Natl. Acad. Sci. U.S.A.* 93, 7950 (1996).
13. K. W. Kinzler and B. Vogelstein, *Cell* 87, 159 (1996).
14. About 50% of the Western population develop colorectal adenomas by the age of 70 [D. Ransohoff and C. Lang, *N. Engl. J. Med.* 325, 37 (1991)] and at least 85% of these tumors contain APC mutations; Y. Miyoshi et al., *Hum Mol Genet* 1, 229–33 (1992); J. Jen et al., *Cancer Res.* 54, 5523 (1994).

15. H. Nagase and Y. Nakamura, *Hum. Mutation* 2, 425 (1993).
16. K. W. Kinzler and B. Vogelstein, *Cell* 87, 159 (1996); S. M. Prescott and R. L. White, ibid., p. 783.
17. G. Joslyn, D. S. Richardson, R. White, T. Alber, *Proc. Natl. Acad. Sci. U. S. A.* 90, 11109 (1993); L. K. Su et al., *Cancer Res.* 53, 2728 (1993).
18. B. Rubinfeld et al., *Science* 262, 1731 (1993); L. K. Su, B. Vogelstein, K. W. Kinzler, ibid., p. 1734.
19. Hulsken, J. Behrens, W. Birchmeier, *Curr. Opin. Cell. Biol.* 6, 711 (1994); B. Rubinfeld, B. Souza, I. Albert, S. Munemitsu, P. Polakis, *J. Biol. Chem.* 270, 5549 (1995).
20. S. Munemitsu et al., *Cancer Res.* 54, 3676 (1994); K. J. Smith et al., ibid. p. 3672.
21. L. K. Su et al., *Cancer Res.* 55, 2972 (1995).
22. A. Matsumine et al., *Science* 272, 1020 (1996).
23. B. Rubinfeld et al., *Science* 272, 1023 (1996).
24. M. Molenaar et al., *Cell* 86, 391 (1996); J. Behrens et al., *Nature* 382, 638 (1996).
25. S. M. Powell et al., *Nature* 359, 235 (1992).
26. D. M. Eccles et al., *Am. J. of Hum. Genet.* 59, 1193 (1996); W. Friedl et al., *Hum Genet* 97, 579 (1996); R. J. Scott et al., *Human Molecular Genetics* 5, 1921 (1996).
27. C. Yost et al., *Genes Dev.* 10, 1443 (1996).
28. S. Munemitsu, I. Albert, B. Rubinfeld, P. Polakis, *Mol Cell Biol* 16, 4088 (1996).
29. M. Peifer, L. M. Pai, M. Casey, *Dev. Biol.* 166, 543 (1994).
30. D J. Kawanishi, et al., *Mol. Cell Biol.* 15, 1175 (1995); P. F. Robbins, et al., *J. Exp. Med.* 183, 1185 (1996).
31. P. J. Morin, B. Vogelstein, K. W. Kinzler, *Proc. Natl. Acad. Sci. U. S. A.* 93, 7950 (1996).
32. J. Groden et al., *Cell* 66, 589 (1991); G. Joslyn et al., ibid., p. 601; K. W. Kinzler et al., *Science* 253, 661 (1991); I. Nisbisho et al., ibid., p. 665.
33. M. Peifer, S. Berg, A. B. Reynolds, *Cell*76, 789 (1994).
34. K. J. Smith et al., *Proc. Natl. Acad. Sci. U. S. A.* 90, 2846 (1993).
35. S. E. Goelz, S. R. Hamilton, B. Vogelstein, *Biochem. Biophys. Res. Commun.* 130, 118 (1985)

We claim:

1. An intron-free DNA molecule encoding Tcf-4 protein as shown in SEQ ID NO:5 or 6.

2. The DNA molecule of claim 1 which has the nucleotide sequence of SEQ ID NO: 1 or 2.

* * * * *

SEQUENCE LISTING

```
(1) GENERAL INFORMATION:

   (iii) NUMBER OF SEQUENCES: 11

(2) INFORMATION FOR SEQ ID NO:1:

     (i) SEQUENCE CHARACTERISTICS:
          (A) LENGTH: 2040 base pairs
          (B) TYPE: nucleic acid
          (C) STRANDEDNESS: single
          (D) TOPOLOGY: linear

    (xi) SEQUENCE DESCRIPTION: SEQ ID NO:1:

ATGCCGCAGC TGAACGGCGG TGGAGGGGAT GACCTAGGCG CCAACGACGA ACTGATTTCC    60

TTCAAAGACG AGGGCGAACA GGAGGAGAAG AGCTCCGAAA ACTCCTCGGC AGAGAGGGAT   120

TTAGCTGATG TCAAATCGTC TCTAGTCAAT GAATCAGAAA CGAATCAAAA CAGCTCCTCC   180

GATTCCGAGG CGGAAAGACG GCCTCCGCCT CGCTCCGAAA GTTTCCGAGA CAAATCCCGG   240

GAAAGTTTGG AAGAAGCGGC CAAGAGGCAA GATGGAGGGC TCTTTAAGGG GCCACCGTAT   300

CCCGGCTACC CCTTCATCAT GATCCCCGAC CTGACGAGCC CCTACCTCCC CAAGCGATCC   360

GTCTCGCCCA CCGCCCGAAC CTATCTCCAG ATGAAATGGC CACTGCTTGA TGTCCAGGCA   420

GGGAGCCTCC AGAGTAGACA AGCCCTCAAG GATGCCCGGT CCCCATCACC GGCACACATT   480

GTCTCTAACA AAGTGCCAGT GGTGCAGCAC CCTCACCATG TCCACCCCCT CACGCCTCTT   540

ATCACGTACA GCAATGAACA CTTCACGCCG GGAAACCCAC CTCCACACTT ACCAGCCGAC   600

GTAGACCCCA AAACAGGAAT CCCACGGCCT CCGCACCCTC CAGATATATC CCCGTATTAC   660

CCACTATCGC CTGGCACCGT AGGACAAATC CCCCATCCGC TAGGATGGTT AGTACCACAG   720

CAAGGTCAAC CAGTGTACCC AATCACGACA GGAGGATTCA GACACCCCTA CCCCACAGCT   780

CTGACCGTCA ATGCTTCCGT GTCCAGGTTC CCTCCCCATA TGGTCCCACC ACATCATACG   840

CTACACACGA CGGGCATTCC GCATCCGGCC ATAGTCACAC CAACAGTCAA ACAGGAATCG   900
```

-continued

```
TCCCAGAGTG ATGTCGGCTC ACTCCATAGT TCAAAGCATC AGGACTCCAA AAAGGAAGAA   960
GAAAAGAAGA AGCCCCACAT AAAGAAACCT CTTAATGCAT TCATGTTGTA TATGAAGGAA  1020
ATGAGAGCAA AGGTCGTAGC TGAGTGCACG TTGAAAGAAA GCGCGGCCAT CAACCAGATC  1080
CTTGGGCGGA GGTGGCATGC ACTGTCCAGA GAAGAGCAAG CGAAATACTA CGAGCTGGCC  1140
CGGAAGGAGC GACAGCTTCA TATGCAACTG TACCCCGGCT GGTCCGCGCG GGATAACTAT  1200
GGAAAGAAGA AGAAGAGGAA AAGGGACAAG CAGCCGGGAG AGACCAATGG AGAAAAAAAA  1260
AGTGCGTTCG CTACATACAA GGTGAAGGCA GCTGCCTCAG CCCACCCTCT TCAGATGGAA  1320
GCTTACTAGA TTCGCCTCCC CCCTCCCCGA ACCTGCTAGG CTCCCCTCCC CGAGACGCCA  1380
AGTCACAGAC TGAGCAGACC CAGCCTCTGT CGCTGTCCCT GAAGCCCGAC CCCCTGGCCC  1440
ACCTGTCCAT GATGCCTCCG CCACCCGCCC TCCTGCTCGC TGAGGCCACC CACAAGGCCT  1500
CCGCCCTCTG TCCCAACGGG GCCCTGGACC TGCCCCCAGC CGCTTTGCAG CCTGCCGCCC  1560
CCTCCTCATC AATTGCACAG CCGTCGACTT CTTGGTTACA TTCCCACAGC TCCCTGGCCG  1620
GGACCCAGCC CCAGCCGCTG TCGCTCGTCA CCAAGTCTTT AGAATAGCTT TAGCGTCGTG  1680
AACCCCGCTG CTTTGTTTAT GGTTTTGTTT CACTTTTCTT AATTTGCCCC CCACCCCCAC  1740
CTTGAAAGGT TTTGTTTTGT ACTCTCTTAA TTTTGTGCCA TGTGGCTACA TTAGTTGATG  1800
TTTATCGAGT TCATTGGTCA ATATTTGACC CATTCTTATT TCAATTTCTC CTTTTAAATA  1860
TGTAGATGAG AGAAGAACCT CATGATTGGT ACCAAAATTT TTATCAACAG CTGTTTAAAG  1920
TCTTTGTAGC GTTTAAAAAA TATATATATA TACATAACTG TTATGTAGTT CGGATAGCTT  1980
AGTTTTAAAA GACTGATTAA AAAACAAAAA AAAAAAAAGC TTGCGAGGGA TCCCCCGGGA  2040
```

(2) INFORMATION FOR SEQ ID NO:2:

(i) SEQUENCE CHARACTERISTICS:
(A) LENGTH: 2444 base pairs
(B) TYPE: nucleic acid
(C) STRANDEDNESS: single
(D) TOPOLOGY: linear (xi) SEQUENCE DESCRIPTION: SEQ ID NO:2:

```
GGTTTTTTTT TTTTACCCCC CTTTTTTATT TATTATTTTT TTGCACATTG AGCGGATCCT    60
TGGGAACGAG AGAAAAAAGA AACCCAAACT CACGCGTGCA GAAGATCTCC CCCCCCTTCC   120
CCTCCCCTCC TCCCTCTTTT CCCCTCCCCA GGAGAAAAAG ACCCCCAAGC AGAAAAAAGT   180
TCACCTTGGA CTCGTCTTTT TCTTGCAATA TTTTTTGGGG GGGCAAAACT TTGAGGGGGT   240
GATTTTTTTT GGCTTTTCTT CCTCCTTCAT TTTTCTTCCA AAATTGCTGC TGGTGGGTGA   300
AAAAAAAATG CCGCAGCTGA ACGGCGGTGG AGGGGATGAC CTAGGCGCCA ACGACGAACT   360
GATTTCCTTC AAAGACGAGG GCGAACAGGA GGAGAAGAGC TCCGAAAACT CCTCGGCAGA   420
GAGGGATTTA GCTGATGTCA AATCGTCTCT AGTCAATGAA TCAGAAACGA ATCAAAACAG   480
CTCCTCCGAT TCCGAGGCGG AAAGACGGCC TCCGCCTCGC TCCGAAAGTT TCCGAGACAA   540
ATCCCGGGAA AGTTTGGAAG AAGCGGCCAA GAGGCAAGAT GGAGGGCTCT TTAAGGGGCC   600
ACCGTATCCC GGCTACCCCT TCATCATGAT CCCCGACCTG ACGAGCCCCT ACCTCCCCAA   660
GCGATCCGTC TCGCCCACCG CCCGAACCTA TCTCCAGATG AAATGGCCAC TGCTTGATGT   720
CCAGGCAGGG AGCCTCCAGA GTAGACAAGC CCTCAAGGAT GCCCGGTCCC CATCACCGGC   780
ACACATTGTC TCTAACAAAG TGCCAGTGGT GCAGCACCCT CACCATGTCC ACCCCCTCAC   840
GCCTCTTATC ACGTACAGCA ATGAACACTT CACGCCGGGA AACCCACCTC CACACTTACC   900
```

-continued

```
AGCCGACGTA GACCCCAAAA CAGGAATCCC ACGGCCTCCG CACCCTCCAG ATATATCCCC   960
GTATTACCCA CTATCGCCTG GCACCGTAGG ACAAATCCCC CATCCGCTAG GATGGTTAGT  1020
ACCACAGCAA GGTCAACCAG TGTACCCAAT CACGACAGGA GGATTCAGAC ACCCCTACCC  1080
CACAGCTCTG ACCGTCAATG CTTCCGTGTC CAGGTTCCCT CCCCATATGG TCCCACCACA  1140
TCATACGCTA CACACGACGG GCATTCCGCA TCCGGCCATA GTCACACCAA CAGTCAAACA  1200
GGAATCGTCC CAGAGTGATG TCGGCTCACT CCATAGTTCA AAGCATCAGG ACTCCAAAAA  1260
GGAAGAAGAA AAGAAGAAGC CCCACATAAA GAAACCTCTT AATGCATTCA TGTTGTATAT  1320
GAAGGAAATG AGAGCAAAGG TCGTAGCTGA GTGCACGTTG AAAGAAAGCG CGGCCATCAA  1380
CCAGATCCTT GGGCGGAGGT GGCATGCACT GTCCAGAGAA GAGCAAGCGA AATACTACGA  1440
GCTGGCCCGG AAGGAGCGAC AGCTTCATAT GCAACTGTAC CCCGGCTGGT CCGCGCGGGA  1500
TAACTATGGA AAGAAGAAGA AGAGGAAAAG GGACAAGCAG CCGGGAGAGA CCAATGAACA  1560
CAGCGAATGT TTCCTAAATC CTTGCCTTTC ACTTCCTCCG ATTACAGACC TCAGCGCTCC  1620
TAAGAAATGC CGAGCGCGCT TTGGCCTTGA TCAACAGAAT AACTGGTGCG GCCCTTGCAG  1680
GAGAAAAAAA AAGTGCGTTC GCTACATACA AGGTGAAGGC AGCTGCCTCA GCCCACCCTC  1740
TTCAGATGGA AGCTTACTAG ATTCGCCTCC CCCCTCCCCG AACCTGCTAG GCTCCCCTCC  1800
CCGAGACGCC AAGTCACAGA CTGAGCAGAC CCAGCCTCTG TCGCTGTCCC TGAAGCCCGA  1860
CCCCCTGGCC CACCTGTCCA TGATGCCTCC GCCACCCGCC CTCCTGCTCG CTGAGGCCAC  1920
CCACAAGGCC TCCGCCCTCT GTCCCAACGG GGCCCTGGAC CTGCCCCCAG CCGCTTTGCA  1980
GCCTGCCGCC CCCTCCTCAT CAATTGCACA GCCGTCGACT TCTTGGTTAC ATTCCCACAG  2040
CTCCCTGGCC GGGACCCAGC CCCAGCCGCT GTCGCTCGTC ACCAAGTCTT TAGAATAGCT  2100
TTAGCGTCGT GAACCCCGCT GCTTTGTTTA TGGTTTTGTT TCACTTTTCT TAATTTGCCC  2160
CCCACCCCCA CCTTGAAAGG TTTTGTTTTG TACTCTCTTA ATTTTGTGCC ATGTGGCTAC  2220
ATTAGTTGAT GTTTATCGAG TTCATTGGTC AATATTTGAC CCATTCTTAT TTCAATTTCT  2280
CCTTTTAAAT ATGTAGATGA GAGAAGAACC TCATGATTGG TACCAAAATT TTTATCAACA  2340
GCTGTTTAAA GTCTTTGTAG CGTTTAAAAA ATATATATAT ATACATAACT GTTATGTAGT  2400
TCGGATAGCT TAGTTTTAAA AGACTGATTA AAAAACAAAA AAAA                   2444
```

(2) INFORMATION FOR SEQ ID NO:3:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:3:

```
CCCTTTGATC TTACC                                                     15
```

(2) INFORMATION FOR SEQ ID NO:4:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:4:

```
CCCTTTGGCC TTACC                                                     15
```

(2) INFORMATION FOR SEQ ID NO:5:

(i) SEQUENCE CHARACTERISTICS:
(A) LENGTH: 442 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:5:

```
Met Pro Gln Leu Asn Gly Gly Gly Gly Asp Asp Leu Gly Ala Asn Asp
 1               5                  10                  15

Glu Leu Ile Ser Phe Lys Asp Glu Gly Glu Gln Glu Glu Lys Ser Ser
            20                  25                  30

Glu Asn Ser Ser Ala Glu Arg Asp Leu Ala Asp Val Lys Ser Ser Leu
        35                  40                  45

Val Asn Glu Ser Glu Thr Asn Gln Asn Ser Ser Ser Asp Ser Glu Ala
    50                  55                  60

Glu Arg Arg Pro Pro Pro Arg Ser Glu Ser Phe Arg Asp Lys Ser Arg
65                  70                  75                  80

Glu Ser Leu Glu Glu Ala Ala Lys Arg Gln Asp Gly Gly Leu Phe Lys
                85                  90                  95

Gly Pro Pro Tyr Pro Gly Tyr Pro Phe Ile Met Ile Pro Asp Leu Thr
            100                 105                 110

Ser Pro Tyr Leu Pro Lys Arg Ser Val Ser Pro Thr Ala Arg Thr Tyr
        115                 120                 125

Leu Gln Met Lys Trp Pro Leu Leu Asp Val Gln Ala Gly Ser Leu Gln
    130                 135                 140

Ser Arg Gln Ala Leu Lys Asp Ala Arg Ser Pro Ser Pro Ala His Ile
145                 150                 155                 160

Val Ser Asn Lys Val Pro Val Val Gln His Pro His His Val His Pro
                165                 170                 175

Leu Thr Pro Leu Ile Thr Tyr Ser Asn Glu His Phe Thr Pro Gly Asn
            180                 185                 190

Pro Pro Pro His Leu Pro Ala Asp Val Asp Pro Lys Thr Gly Ile Pro
        195                 200                 205

Arg Pro Pro His Pro Pro Asp Ile Ser Pro Tyr Tyr Pro Leu Ser Pro
    210                 215                 220

Gly Thr Val Gly Gln Ile Pro His Pro Leu Gly Trp Leu Val Pro Gln
225                 230                 235                 240

Gln Gly Gln Pro Val Tyr Pro Ile Thr Thr Gly Gly Phe Arg His Pro
                245                 250                 255

Tyr Pro Thr Ala Leu Thr Val Asn Ala Ser Val Ser Arg Phe Pro Pro
            260                 265                 270

His Met Val Pro Pro His His Thr Leu His Thr Thr Gly Ile Pro His
        275                 280                 285

Pro Ala Ile Val Thr Pro Thr Val Lys Gln Glu Ser Ser Gln Ser Asp
    290                 295                 300

Val Gly Ser Leu His Ser Ser Lys His Gln Asp Ser Lys Lys Glu Glu
305                 310                 315                 320

Glu Lys Lys Lys Pro His Ile Lys Lys Pro Leu Asn Ala Phe Met Leu
                325                 330                 335

Tyr Met Lys Glu Met Arg Ala Lys Val Val Ala Glu Cys Thr Leu Lys
            340                 345                 350

Glu Ser Ala Ala Ile Asn Gln Ile Leu Gly Arg Arg Trp His Ala Leu
```

```
        355                 360                 365

Ser Arg Glu Glu Gln Ala Lys Tyr Tyr Glu Leu Ala Arg Lys Glu Arg
    370                 375                 380

Gln Leu His Met Gln Leu Tyr Pro Gly Trp Ser Ala Arg Asp Asn Tyr
385                 390                 395                 400

Gly Lys Lys Lys Lys Arg Lys Arg Asp Lys Gln Pro Gly Glu Thr Asn
                405                 410                 415

Gly Glu Lys Lys Ser Ala Phe Ala Thr Tyr Lys Val Lys Ala Ala Ala
            420                 425                 430

Ser Ala His Pro Leu Gln Met Glu Ala Tyr
        435                 440
```

(2) INFORMATION FOR SEQ ID NO:6:

(i) SEQUENCE CHARACTERISTICS:
(A) LENGTH: 596 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:6:

```
Met Pro Gln Leu Asn Gly Gly Gly Gly Asp Asp Leu Gly Ala Asn Asp
 1               5                  10                  15

Glu Leu Ile Ser Phe Lys Asp Glu Gly Glu Gln Glu Glu Lys Ser Ser
            20                  25                  30

Glu Asn Ser Ser Ala Glu Arg Asp Leu Ala Asp Val Lys Ser Ser Leu
        35                  40                  45

Val Asn Glu Ser Glu Thr Asn Gln Asn Ser Ser Ser Asp Ser Glu Ala
    50                  55                  60

Glu Arg Arg Pro Pro Pro Arg Ser Glu Ser Phe Arg Asp Lys Ser Arg
65                  70                  75                  80

Glu Ser Leu Glu Glu Ala Ala Lys Arg Gln Asp Gly Gly Leu Phe Lys
                85                  90                  95

Gly Pro Pro Tyr Pro Gly Tyr Pro Phe Ile Met Ile Pro Asp Leu Thr
            100                 105                 110

Ser Pro Tyr Leu Pro Asn Gly Ser Val Ser Pro Thr Ala Arg Thr Tyr
        115                 120                 125

Leu Gln Met Lys Trp Pro Leu Leu Asp Val Gln Ala Gly Ser Leu Gln
    130                 135                 140

Ser Arg Gln Ala Leu Lys Asp Ala Arg Ser Pro Ser Pro Ala His Ile
145                 150                 155                 160

Val Ser Asn Lys Val Pro Val Val Gln His Pro His His Val His Pro
                165                 170                 175

Leu Thr Pro Leu Ile Thr Tyr Ser Asn Glu His Phe Thr Pro Gly Asn
            180                 185                 190

Pro Pro Pro His Leu Pro Ala Asp Val Asp Pro Lys Thr Gly Ile Pro
        195                 200                 205

Arg Pro Pro His Pro Pro Asp Ile Ser Pro Tyr Tyr Pro Leu Ser Pro
    210                 215                 220

Gly Thr Val Gly Gln Ile Pro His Pro Leu Gly Trp Leu Val Pro Gln
225                 230                 235                 240

Gln Gly Gln Pro Val Tyr Pro Ile Thr Thr Gly Gly Phe Arg His Pro
                245                 250                 255

Tyr Pro Thr Ala Leu Thr Val Asn Ala Ser Val Ser Arg Phe Pro Pro
            260                 265                 270
```

```
His Met Val Pro Pro His His Thr Leu His Thr Thr Gly Ile Pro His
        275                 280                 285

Pro Ala Ile Val Thr Pro Thr Val Lys Gln Glu Ser Ser Gln Ser Asp
    290                 295                 300

Val Gly Ser Leu His Ser Ser Lys His Gln Asp Ser Lys Lys Glu Glu
305                 310                 315                 320

Glu Lys Lys Lys Pro His Ile Lys Lys Pro Leu Asn Ala Phe Met Leu
                325                 330                 335

Tyr Met Lys Glu Met Arg Ala Lys Val Val Ala Glu Cys Thr Leu Lys
            340                 345                 350

Glu Ser Ala Ala Ile Asn Gln Ile Leu Gly Arg Arg Trp His Ala Leu
        355                 360                 365

Ser Arg Glu Glu Gln Ala Lys Tyr Tyr Glu Leu Ala Arg Lys Glu Arg
    370                 375                 380

Gln Leu His Met Gln Leu Tyr Pro Gly Trp Ser Ala Arg Asp Asn Tyr
385                 390                 395                 400

Gly Lys Lys Lys Lys Arg Lys Arg Asp Lys Gln Pro Gly Glu Thr Asn
                405                 410                 415

Glu His Ser Glu Cys Phe Leu Asn Pro Cys Leu Ser Leu Pro Pro Ile
            420                 425                 430

Thr Asp Leu Ser Ala Pro Lys Lys Cys Arg Ala Arg Phe Gly Leu Asp
        435                 440                 445

Gln Gln Asn Asn Trp Cys Gly Pro Cys Arg Arg Lys Lys Lys Cys Val
    450                 455                 460

Arg Tyr Ile Gln Gly Glu Gly Ser Cys Leu Ser Pro Pro Ser Ser Asp
465                 470                 475                 480

Gly Ser Leu Leu Asp Ser Pro Pro Pro Ser Pro Asn Leu Leu Gly Ser
                485                 490                 495

Pro Pro Arg Asp Ala Lys Ser Gln Thr Glu Gln Thr Gln Pro Leu Ser
            500                 505                 510

Leu Ser Leu Lys Pro Asp Pro Leu Ala His Leu Ser Met Met Pro Pro
        515                 520                 525

Pro Pro Ala Leu Leu Leu Ala Glu Ala Thr His Lys Ala Ser Ala Leu
    530                 535                 540

Cys Pro Asn Gly Ala Leu Asp Leu Pro Pro Ala Ala Leu Gln Pro Ala
545                 550                 555                 560

Ala Pro Ser Ser Ser Ile Ala Gln Pro Ser Thr Ser Trp Leu His Ser
                565                 570                 575

His Ser Ser Leu Ala Gly Thr Gln Pro Gln Pro Leu Ser Leu Val Thr
            580                 585                 590

Lys Ser Leu Glu
        595
```

(2) INFORMATION FOR SEQ ID NO:7:

(i) SEQUENCE CHARACTERISTICS:
(A) LENGTH: 2973 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:7:

```
Met Ala Ala Ala Ser Tyr Asp Gln Leu Leu Lys Gln Val Glu Ala Leu
 1              5                  10                  15
```

-continued

```
Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu
        35                  40                  45

Lys Gln Leu Gln Gly Ser Ile Glu Asp Glu Ala Met Ala Ser Ser Gly
    50                  55                  60

Gln Ile Asp Leu Leu Glu Arg Leu Lys Glu Leu Asn Leu Asp Ser Ser
65                  70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
            100                 105                 110

Val Pro Met Gly Ser Phe Pro Arg Arg Gly Phe Val Asn Gly Ser Arg
        115                 120                 125

Glu Ser Thr Gly Tyr Leu Glu Glu Leu Glu Lys Glu Arg Ser Leu Leu
    130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Met Thr Arg Arg Gln Leu Glu Tyr Glu
            180                 185                 190

Ala Arg Gln Ile Arg Val Ala Met Glu Glu Gln Leu Gly Thr Cys Gln
        195                 200                 205

Asp Met Glu Lys Arg Ala Gln Arg Arg Ile Ala Arg Ile Gln Gln Ile
    210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
            260                 265                 270

Thr Ser Gly Asn Gly Gln Gly Ser Thr Thr Arg Met Asp His Glu Thr
        275                 280                 285

Ala Ser Val Leu Ser Ser Ser Ser Thr His Ser Ala Pro Arg Arg Leu
    290                 295                 300

Thr Ser His Leu Gly Thr Lys Val Glu Met Val Tyr Ser Leu Leu Ser
305                 310                 315                 320

Met Leu Gly Thr His Asp Lys Asp Asp Met Ser Arg Thr Leu Leu Ala
                325                 330                 335

Met Ser Ser Ser Gln Asp Ser Cys Ile Ser Met Arg Gln Ser Gly Cys
            340                 345                 350

Leu Pro Leu Leu Ile Gln Leu Leu His Gly Asn Asp Lys Asp Ser Val
        355                 360                 365

Leu Leu Gly Asn Ser Arg Gly Ser Lys Glu Ala Arg Ala Arg Ala Ser
    370                 375                 380

Ala Ala Leu His Asn Ile Ile His Ser Gln Pro Asp Asp Lys Arg Gly
385                 390                 395                 400

Arg Arg Glu Ile Arg Val Leu His Leu Leu Glu Gln Ile Arg Ala Tyr
                405                 410                 415

Cys Glu Thr Cys Trp Glu Trp Gln Glu Ala His Glu Pro Gly Met Asp
            420                 425                 430

Gln Asp Lys Asn Pro Met Pro Ala Pro Val Glu His Gln Ile Cys Pro
        435                 440                 445
```

-continued

```
Ala Val Cys Val Leu Met Lys Leu Ser Phe Asp Glu Glu His Arg His
    450                 455                 460

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
                485                 490                 495

Leu Arg Arg Tyr Ala Gly Met Ala Leu Thr Asn Leu Thr Phe Gly Asp
            500                 505                 510

Val Ala Asn Lys Ala Thr Leu Cys Ser Met Lys Gly Cys Met Arg Ala
        515                 520                 525

Leu Val Ala Gln Leu Lys Ser Glu Ser Glu Asp Leu Gln Gln Val Ile
    530                 535                 540

Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
                565                 570                 575

Leu Glu Val Lys Lys Glu Ser Thr Leu Lys Ser Val Leu Ser Ala Leu
            580                 585                 590

Trp Asn Leu Ser Ala His Cys Thr Glu Asn Lys Ala Asp Ile Cys Ala
        595                 600                 605

Val Asp Gly Ala Leu Ala Phe Leu Val Gly Thr Leu Thr Tyr Arg Ser
    610                 615                 620

Gln Thr Asn Thr Leu Ala Ile Ile Glu Ser Gly Gly Gly Ile Leu Arg
625                 630                 635                 640

Asn Val Ser Ser Leu Ile Ala Thr Asn Glu Asp His Arg Gln Ile Leu
                645                 650                 655

Arg Glu Asn Asn Cys Leu Gln Thr Leu Leu Gln His Leu Lys Ser His
            660                 665                 670

Ser Leu Thr Ile Val Ser Asn Ala Cys Gly Thr Leu Trp Asn Leu Ser
        675                 680                 685

Ala Arg Asn Pro Lys Asp Gln Glu Ala Leu Trp Asp Met Gly Ala Val
    690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
            740                 745                 750

His Val Arg Lys Gln Lys Ala Leu Glu Ala Glu Leu Asp Ala Gln His
        755                 760                 765

Leu Ser Glu Thr Phe Asp Asn Ile Asp Asn Leu Ser Pro Lys Ala Ser
    770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
            820                 825                 830

Ser Ser Ser Ser Ser Arg Gly Ser Leu Asp Ser Ser Arg Ser Glu Lys
        835                 840                 845

Asp Arg Ser Leu Glu Arg Glu Arg Gly Ile Gly Leu Gly Asn Tyr His
    850                 855                 860

Pro Ala Thr Glu Asn Pro Gly Thr Ser Ser Lys Arg Gly Leu Gln Ile
```

-continued

```
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
        915                 920                 925

His Thr His Ser Asn Thr Tyr Asn Phe Thr Lys Ser Glu Asn Ser Asn
    930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Ser Asp Gly Tyr Gly Lys Arg
                965                 970                 975

Gly Gln Met Lys Pro Ser Ile Glu Ser Tyr Ser Glu Asp Asp Glu Ser
            980                 985                 990

Lys Phe Cys Ser Tyr Gly Gln Tyr Pro Ala Asp Leu Ala His Lys Ile
        995                 1000                1005

His Ser Ala Asn His Met Asp Asp Asn Asp Gly Glu Leu Asp Thr Pro
   1010                1015                1020

Ile Asn Tyr Ser Leu Lys Tyr Ser Asp Glu Gln Leu Asn Ser Gly Arg
025                1030                1035                1040

Gln Ser Pro Ser Gln Asn Glu Arg Trp Ala Arg Pro Lys His Ile Ile
               1045                1050                1055

Glu Asp Glu Ile Lys Gln Ser Glu Gln Arg Gln Ser Arg Asn Gln Ser
           1060                1065                1070

Thr Thr Tyr Pro Val Tyr Thr Glu Ser Thr Asp Asp Lys His Leu Lys
       1075                1080                1085

Phe Gln Pro His Phe Gly Gln Gln Glu Cys Val Ser Pro Tyr Arg Ser
   1090                1095                1100

Arg Gly Ala Asn Gly Ser Glu Thr Asn Arg Val Gly Ser Asn His Gly
105                1110                1115                1120

Ile Asn Gln Asn Val Ser Gln Ser Leu Cys Gln Glu Asp Asp Tyr Glu
               1125                1130                1135

Asp Asp Lys Pro Thr Asn Tyr Ser Glu Arg Tyr Ser Glu Glu Glu Gln
           1140                1145                1150

His Glu Glu Glu Glu Arg Pro Thr Asn Tyr Ser Ile Lys Tyr Asn Glu
       1155                1160                1165

Glu Lys Arg His Val Asp Gln Pro Ile Asp Tyr Ser Leu Lys Tyr Ala
   1170                1175                1180

Thr Asp Ile Pro Ser Ser Gln Lys Gln Ser Phe Ser Phe Ser Lys Ser
185                1190                1195                1200

Ser Ser Gly Gln Ser Ser Lys Thr Glu His Met Ser Ser Ser Ser Glu
               1205                1210                1215

Asn Thr Ser Thr Pro Ser Ser Asn Ala Lys Arg Gln Asn Gln Leu His
           1220                1225                1230

Pro Ser Ser Ala Gln Ser Arg Ser Gly Gln Pro Gln Lys Ala Ala Thr
       1235                1240                1245

Cys Lys Val Ser Ser Ile Asn Gln Glu Thr Ile Gln Thr Tyr Cys Val
   1250                1255                1260

Glu Asp Thr Pro Ile Cys Phe Ser Arg Cys Ser Ser Leu Ser Ser Leu
265                1270                1275                1280

Ser Ser Ala Glu Asp Glu Ile Gly Cys Asn Gln Thr Thr Gln Glu Ala
               1285                1290                1295
```

-continued

```
Asp Ser Ala Asn Thr Leu Gln Ile Ala Glu Ile Lys Glu Lys Ile Gly
          1300                1305                1310

Thr Arg Ser Ala Glu Asp Pro Val Ser Glu Val Pro Ala Val Ser Gln
      1315                1320                1325

His Pro Arg Thr Lys Ser Ser Arg Leu Gln Gly Ser Ser Leu Ser Ser
   1330                1335                1340

Glu Ser Ala Arg His Lys Ala Val Glu Phe Ser Ser Gly Ala Lys Ser
345                1350                1355                1360

Pro Ser Lys Ser Gly Ala Gln Thr Pro Lys Ser Pro Pro Glu His Tyr
              1365                1370                1375

Val Gln Glu Thr Pro Leu Met Phe Ser Arg Cys Thr Ser Val Ser Ser
          1380                1385                1390

Leu Asp Ser Phe Glu Ser Arg Ser Ile Ala Ser Ser Val Gln Ser Glu
      1395                1400                1405

Pro Cys Ser Gly Met Val Ser Gly Ile Ile Ser Pro Ser Asp Leu Pro
   1410                1415                1420

Asp Ser Pro Gly Gln Thr Met Pro Pro Ser Arg Ser Lys Thr Pro Pro
425                1430                1435                1440

Pro Pro Pro Gln Thr Ala Gln Thr Lys Arg Glu Val Pro Lys Asn Lys
              1445                1450                1455

Ala Pro Thr Ala Glu Lys Arg Glu Ser Gly Pro Lys Gln Ala Ala Val
          1460                1465                1470

Asn Ala Ala Val Gln Arg Val Gln Val Leu Pro Asp Ala Asp Thr Leu
      1475                1480                1485

Leu His Phe Ala Thr Glu Ser Thr Pro Asp Gly Phe Ser Cys Ser Ser
   1490                1495                1500

Ser Leu Ser Ala Leu Ser Leu Asp Glu Pro Phe Ile Gln Lys Asp Val
505                1510                1515                1520

Glu Leu Arg Ile Met Pro Pro Val Gln Glu Asn Asp Asn Gly Asn Glu
              1525                1530                1535

Thr Glu Ser Glu Gln Pro Lys Glu Ser Asn Glu Asn Gln Glu Lys Glu
          1540                1545                1550

Ala Glu Lys Thr Ile Asp Ser Glu Lys Asp Leu Leu Asp Asp Ser Asp
      1555                1560                1565

Asp Asp Asp Ile Glu Ile Leu Glu Glu Cys Ile Ile Ser Ala Met Pro
   1570                1575                1580

Thr Lys Ser Ser Arg Lys Ala Lys Lys Pro Ala Gln Thr Ala Ser Lys
585                1590                1595                1600

Leu Pro Pro Pro Val Ala Arg Lys Pro Ser Gln Leu Pro Val Tyr Lys
              1605                1610                1615

Leu Leu Pro Ser Gln Asn Arg Leu Gln Pro Gln Lys His Val Ser Phe
          1620                1625                1630

Thr Pro Gly Asp Asp Met Pro Arg Val Tyr Cys Val Glu Gly Thr Pro
      1635                1640                1645

Ile Asn Phe Ser Thr Ala Thr Ser Leu Ser Asp Leu Thr Ile Glu Ser
   1650                1655                1660

Pro Pro Asn Glu Leu Ala Ala Gly Glu Gly Val Arg Gly Gly Ala Gln
665                1670                1675                1680

Ser Gly Glu Phe Glu Lys Arg Asp Thr Ile Pro Thr Glu Gly Arg Ser
              1685                1690                1695

Thr Asp Glu Ala Gln Gly Gly Lys Thr Ser Ser Val Thr Ile Pro Glu
          1700                1705                1710

Leu Asp Asp Asn Lys Ala Glu Glu Gly Asp Ile Leu Ala Glu Cys Ile
      1715                1720                1725
```

-continued

```
Asn Ser Ala Met Pro Lys Gly Lys Ser His Lys Pro Phe Arg Val Lys
   1730                1735                1740

Lys Ile Met Asp Gln Val Gln Gln Ala Ser Ala Ser Ser Ser Ala Pro
745                 1750                1755                1760

Asn Lys Asn Gln Leu Asp Gly Lys Lys Lys Lys Pro Thr Ser Pro Val
               1765                1770                1775

Lys Pro Ile Pro Gln Asn Thr Glu Tyr Arg Thr Arg Val Arg Lys Asn
           1780                1785                1790

Ala Asp Ser Lys Asn Asn Leu Asn Ala Glu Arg Val Phe Ser Asp Asn
       1795                1800                1805

Lys Asp Ser Lys Lys Gln Asn Leu Lys Asn Asn Ser Lys Asp Phe Asn
   1810                1815                1820

Asp Lys Leu Pro Asn Asn Glu Asp Arg Val Arg Gly Ser Phe Ala Phe
825                 1830                1835                1840

Asp Ser Pro His His Tyr Thr Pro Ile Glu Gly Thr Pro Tyr Cys Phe
               1845                1850                1855

Ser Arg Asn Asp Ser Leu Ser Ser Leu Asp Phe Asp Asp Asp Asp Val
           1860                1865                1870

Asp Leu Ser Arg Glu Lys Ala Glu Leu Arg Lys Ala Lys Glu Asn Lys
       1875                1880                1885

Glu Ser Glu Ala Lys Val Thr Ser His Thr Glu Leu Thr Ser Asn Gln
   1890                1895                1900

Gln Ser Ala Asn Lys Thr Gln Ala Ile Ala Lys Gln Pro Ile Asn Arg
905                 1910                1915                1920

Gly Gln Pro Lys Pro Ile Leu Gln Lys Gln Ser Thr Phe Pro Gln Ser
               1925                1930                1935

Ser Lys Asp Ile Pro Asp Arg Gly Ala Ala Thr Asp Glu Lys Leu Gln
           1940                1945                1950

Asn Phe Ala Ile Glu Asn Thr Pro Val Cys Phe Ser His Asn Ser Ser
       1955                1960                1965

Leu Ser Ser Leu Ser Asp Ile Asp Gln Glu Asn Asn Asn Lys Glu Asn
   1970                1975                1980

Glu Pro Ile Lys Glu Thr Glu Pro Pro Asp Ser Gln Gly Glu Pro Ser
985                 1990                1995                2000

Lys Pro Gln Ala Ser Gly Tyr Ala Pro Lys Ser Phe His Val Glu Asp
               2005                2010                2015

Thr Pro Val Cys Phe Ser Arg Asn Ser Ser Leu Ser Ser Leu Ser Ile
           2020                2025                2030

Asp Ser Glu Asp Asp Leu Leu Gln Glu Cys Ile Ser Ser Ala Met Pro
       2035                2040                2045

Lys Lys Lys Lys Pro Ser Arg Leu Lys Gly Asp Asn Glu Lys His Ser
   2050                2055                2060

Pro Arg Asn Met Gly Gly Ile Leu Gly Glu Asp Leu Thr Leu Asp Leu
065                 2070                2075                2080

Lys Asp Ile Gln Arg Pro Asp Ser Glu His Gly Leu Ser Pro Asp Ser
               2085                2090                2095

Glu Asn Phe Asp Trp Lys Ala Ile Gln Glu Gly Ala Asn Ser Ile Val
           2100                2105                2110

Ser Ser Leu His Gln Ala Ala Ala Ala Ala Cys Leu Ser Arg Gln Ala
       2115                2120                2125

Ser Ser Asp Ser Asp Ser Ile Leu Ser Leu Lys Ser Gly Ile Ser Leu
   2130                2135                2140

Gly Ser Pro Phe His Leu Thr Pro Asp Gln Glu Glu Lys Pro Phe Thr
```

-continued

```
145                 2150                2155                2160

Ser Asn Lys Gly Pro Arg Ile Leu Lys Pro Gly Glu Lys Ser Thr Leu
                2165                2170                2175

Glu Thr Lys Lys Ile Glu Ser Glu Ser Lys Gly Ile Lys Gly Gly Lys
            2180                2185                2190

Lys Val Tyr Lys Ser Leu Ile Thr Gly Lys Val Arg Ser Asn Ser Glu
        2195                2200                2205

Ile Ser Gly Gln Met Lys Gln Pro Leu Gln Ala Asn Met Pro Ser Ile
    2210                2215                2220

Ser Arg Gly Arg Thr Met Ile His Ile Pro Gly Val Arg Asn Ser Ser
225                 2230                2235                2240

Ser Ser Thr Ser Pro Val Ser Lys Lys Gly Pro Pro Leu Lys Thr Pro
                2245                2250                2255

Ala Ser Lys Ser Pro Ser Glu Gly Gln Thr Ala Thr Thr Ser Pro Arg
            2260                2265                2270

Gly Ala Lys Pro Ser Val Lys Ser Glu Leu Ser Pro Val Ala Arg Gln
        2275                2280                2285

Thr Ser Gln Ile Gly Gly Ser Ser Lys Ala Pro Ser Arg Ser Gly Ser
    2290                2295                2300

Arg Asp Ser Thr Pro Ser Arg Pro Ala Gln Gln Pro Leu Ser Arg Pro
305                 2310                2315                2320

Ile Gln Ser Pro Gly Arg Asn Ser Ile Ser Pro Gly Arg Asn Gly Ile
                2325                2330                2335

Ser Pro Pro Asn Lys Leu Ser Gln Leu Pro Arg Thr Ser Ser Pro Ser
            2340                2345                2350

Thr Ala Ser Thr Lys Ser Ser Gly Ser Gly Lys Met Ser Tyr Thr Ser
        2355                2360                2365

Pro Gly Arg Gln Met Ser Gln Gln Asn Leu Thr Lys Gln Thr Gly Leu
    2370                2375                2380

Ser Lys Asn Ala Ser Ser Ile Pro Arg Ser Glu Ser Ala Ser Lys Gly
385                 2390                2395                2400

Leu Asn Gln Met Asn Asn Gly Asn Gly Ala Asn Lys Lys Val Glu Leu
                2405                2410                2415

Ser Arg Met Ser Ser Thr Lys Ser Ser Gly Ser Glu Ser Asp Arg Ser
            2420                2425                2430

Glu Arg Pro Val Leu Val Arg Gln Ser Thr Phe Ile Lys Glu Ala Pro
        2435                2440                2445

Ser Pro Thr Leu Arg Arg Lys Leu Glu Glu Ser Ala Ser Phe Glu Ser
    2450                2455                2460

Leu Ser Pro Ser Ser Arg Pro Ala Ser Pro Thr Arg Ser Gln Ala Gln
465                 2470                2475                2480

Thr Pro Val Leu Ser Pro Ser Leu Pro Asp Met Ser Leu Ser Thr His
                2485                2490                2495

Ser Ser Val Gln Ala Gly Gly Trp Arg Lys Leu Pro Pro Asn Leu Ser
            2500                2505                2510

Pro Thr Ile Glu Tyr Asn Asp Gly Arg Pro Ala Lys Arg His Asp Ile
        2515                2520                2525

Ala Arg Ser His Ser Glu Ser Pro Ser Arg Leu Pro Ile Asn Arg Ser
    2530                2535                2540

Gly Thr Trp Lys Arg Glu His Ser Lys His Ser Ser Ser Leu Pro Arg
545                 2550                2555                2560

Val Ser Thr Trp Arg Arg Thr Gly Ser Ser Ser Ser Ile Leu Ser Ala
                2565                2570                2575
```

-continued

Ser Ser Glu Ser Ser Glu Lys Ala Lys Ser Glu Asp Glu Lys His Val
2580 2585 2590

Asn Ser Ile Ser Gly Thr Lys Gln Ser Lys Glu Asn Gln Val Ser Ala
2595 2600 2605

Lys Gly Thr Trp Arg Lys Ile Lys Glu Asn Glu Phe Ser Pro Thr Asn
2610 2615 2620

Ser Thr Ser Gln Thr Val Ser Ser Gly Ala Thr Asn Gly Ala Glu Ser
625 2630 2635 2640

Lys Thr Leu Ile Tyr Gln Met Ala Pro Ala Val Ser Lys Thr Glu Asp
2645 2650 2655

Val Trp Val Arg Ile Glu Asp Cys Pro Ile Asn Asn Pro Arg Ser Gly
2660 2665 2670

Arg Ser Pro Thr Gly Asn Thr Pro Pro Val Ile Asp Ser Val Ser Glu
2675 2680 2685

Lys Ala Asn Pro Asn Ile Lys Asp Ser Lys Asp Asn Gln Ala Lys Gln
2690 2695 2700

Asn Val Gly Asn Gly Ser Val Pro Met Arg Thr Val Gly Leu Glu Asn
705 2710 2715 2720

Arg Leu Asn Ser Phe Ile Gln Val Asp Ala Pro Asp Gln Lys Gly Thr
2725 2730 2735

Glu Ile Lys Pro Gly Gln Asn Asn Pro Val Pro Val Ser Glu Thr Asn
2740 2745 2750

Glu Ser Ser Ile Val Glu Arg Thr Pro Phe Ser Ser Ser Ser Ser Ser
2755 2760 2765

Lys His Ser Ser Pro Ser Gly Thr Val Ala Ala Arg Val Thr Pro Phe
2770 2775 2780

Asn Tyr Asn Pro Ser Pro Arg Lys Ser Ser Ala Asp Ser Thr Ser Ala
785 2790 2795 2800

Arg Pro Ser Gln Ile Pro Thr Pro Val Asn Asn Asn Thr Lys Lys Arg
2805 2810 2815

Asp Ser Lys Thr Asp Ser Thr Glu Ser Ser Gly Thr Gln Ser Pro Lys
2820 2825 2830

Arg His Ser Gly Ser Tyr Leu Val Thr Ser Val Lys Arg Gly Arg Met
2835 2840 2845

Lys Leu Arg Lys Phe Tyr Val Asn Tyr Asn Cys Tyr Ile Asp Ile Leu
2850 2855 2860

Phe Gln Met Lys Leu Lys Thr Glu Lys Phe Cys Lys Val Phe Leu Leu
865 2870 2875 2880

Glu Gly Phe Cys Ser Gly Ser His Ile Tyr Thr Leu Ser Ser Leu Val
2885 2890 2895

Leu Phe Trp Glu Ala Leu Leu Met Val Arg Lys Lys Ile Val Lys Pro
2900 2905 2910

Ser Met Phe Val Gln Tyr Val Leu His Val Phe Lys Val Ala Pro Ile
2915 2920 2925

Pro Thr Ser Phe Asn Tyr Cys Leu Ser Asn Asn Glu His Tyr Arg Lys
2930 2935 2940

Ile Tyr Ile Ala Val Ile Asn His Phe Ile Ile Asn Leu Asn Leu His
945 2950 2955 2960

Gln Gly Lys Ile Gly Ile Tyr Ala Lys Lys Asn Val Phe
2965 2970

(2) INFORMATION FOR SEQ ID NO:8:

(i) SEQUENCE CHARACTERISTICS:
(A) LENGTH: 486 amino acids (B) TYPE: amino acid
(C) STRANDEDNESS: single
(D) TOPOLOGY: linear (ii) MOLECULE TYPE: None (xi) SEQUENCE DESCRIPTION: SEQ ID NO:8:

```
Met Pro Gln Leu Asp Ser Gly Gly Gly Gly Ala Gly Gly Gly Asp Asp
 1              5                  10                  15

Leu Gly Ala Pro Asp Glu Leu Leu Ala Phe Gln Asp Glu Gly Glu Glu
            20                  25                  30

Gln Asp Asp Lys Ser Arg Asp Ser Ala Gly Pro Glu Arg Asp Leu Ala
        35                  40                  45

Glu Leu Lys Ser Ser Leu Val Asn Glu Ser Glu Gly Ala Ala Gly Ser
    50                  55                  60

Ala Gly Ile Pro Gly Val Pro Gly Ala Gly Ala Gly Ala Arg Gly Glu
65                  70                  75                  80

Ala Glu Ala Leu Gly Arg Glu His Arg Ala Gln Arg Leu Phe Pro Asp
                85                  90                  95

Lys Leu Pro Glu Pro Leu Glu Asp Gly Leu Lys Ala Pro Glu Cys Thr
            100                 105                 110

Ser Gly Met Tyr Lys Glu Thr Val Tyr Ser Ala Phe Asn Leu Leu Met
        115                 120                 125

His Tyr Pro Pro Pro Ser Gly Ala Gly Gln His Pro Gln Pro Gln Pro
    130                 135                 140

Pro Leu His Lys Ala Asn Gln Pro Pro His Gly Val Pro Gln Leu Ser
145                 150                 155                 160

Leu Tyr Glu His Phe Asn Ser Pro His Pro Thr Pro Ala Pro Ala Asp
                165                 170                 175

Ile Ser Gln Lys Gln Val His Arg Pro Leu Gln Thr Pro Asp Leu Ser
            180                 185                 190

Gly Phe Tyr Ser Leu Thr Ser Gly Ser Met Gly Gln Leu Pro His Thr
        195                 200                 205

Val Ser Trp Pro Ser Pro Pro Leu Tyr Pro Leu Ser Pro Ser Cys Gly
    210                 215                 220

Tyr Arg Gln His Phe Pro Ala Pro Thr Ala Ala Pro Gly Ala Pro Tyr
225                 230                 235                 240

Pro Arg Phe Thr His Pro Ser Leu Met Leu Gly Ser Gly Val Pro Gly
                245                 250                 255

His Pro Ala Ala Ile Pro His Pro Ala Ile Val Pro Pro Ser Gly Lys
            260                 265                 270

Gln Glu Leu Gln Pro Phe Asp Arg Asn Leu Lys Thr Gln Ala Glu Ser
        275                 280                 285

Lys Ala Glu Lys Glu Ala Lys Lys Pro Thr Ile Lys Lys Pro Leu Asn
    290                 295                 300

Ala Phe Met Leu Tyr Met Lys Glu Met Arg Ala Lys Val Ile Ala Glu
305                 310                 315                 320

Cys Thr Leu Lys Glu Ser Ala Ala Ile Asn Gln Ile Leu Gly Arg Arg
                325                 330                 335

Trp His Ala Leu Ser Arg Glu Glu Gln Ala Lys Tyr Tyr Glu Leu Ala
            340                 345                 350

Arg Lys Glu Arg Gln Leu His Met Gln Leu Tyr Pro Gly Trp Ser Ala
        355                 360                 365

Arg Asp Asn Tyr Gly Lys Lys Lys Arg Arg Ser Arg Glu Lys His Gln
    370                 375                 380
```

-continued

```
Glu Ser Thr Thr Gly Gly Lys Arg Asn Ala Phe Gly Thr Tyr Pro Glu
385                 390                 395                 400

Lys Ala Ala Ala Pro Ala Pro Phe Leu Pro Met Thr Val Leu Ala Ala
                405                 410                 415

Pro Gly Pro Gln Leu Pro Arg Thr His Pro His Thr Ile Cys Cys Pro
            420                 425                 430

Ala Ser Pro Gln Asn Cys Leu Leu Ala Leu Arg Ser Arg His Leu His
        435                 440                 445

Pro Gln Val Ser Pro Leu Leu Ser Ala Ser Gln Pro Gln Gly Pro His
    450                 455                 460

Arg Pro Pro Ala Ala Pro Cys Arg Ala His Arg Tyr Ser Asn Arg Asn
465                 470                 475                 480

Leu Arg Asp Arg Trp Pro
                485
```

(2) INFORMATION FOR SEQ ID NO:9:

(i) SEQUENCE CHARACTERISTICS:
(A) LENGTH: 511 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:9:

```
Met Pro Gln Leu Asp Ser Gly Gly Gly Gly Ala Gly Gly Gly Asp Asp
 1               5                  10                  15

Leu Gly Ala Pro Asp Glu Leu Leu Ala Phe Gln Asp Glu Gly Glu Glu
            20                  25                  30

Gln Asp Asp Lys Ser Arg Asp Ser Ala Gly Pro Glu Arg Asp Leu Ala
        35                  40                  45

Glu Leu Lys Ser Ser Leu Val Asn Glu Ser Glu Gly Ala Ala Gly Ser
    50                  55                  60

Ala Gly Ile Pro Gly Val Pro Gly Ala Gly Ala Gly Ala Arg Gly Glu
65                  70                  75                  80

Ala Glu Ala Leu Gly Arg Glu His Arg Ala Gln Arg Leu Phe Pro Asp
                85                  90                  95

Lys Leu Pro Glu Pro Leu Glu Asp Gly Leu Lys Ala Pro Glu Cys Thr
            100                 105                 110

Ser Gly Met Tyr Lys Glu Thr Val Tyr Ser Ala Phe Asn Leu Leu Met
        115                 120                 125

His Tyr Pro Pro Pro Ser Gly Ala Gly Gln His Pro Gln Pro Gln Pro
    130                 135                 140

Pro Leu His Lys Ala Asn Gln Pro Pro His Gly Val Pro Gln Leu Ser
145                 150                 155                 160

Leu Tyr Glu His Phe Asn Ser Pro His Pro Thr Pro Ala Pro Ala Asp
                165                 170                 175

Ile Ser Gln Lys Gln Val His Arg Pro Leu Gln Thr Pro Asp Leu Ser
            180                 185                 190

Gly Phe Tyr Ser Leu Thr Ser Gly Ser Met Gly Gln Leu Pro His Thr
        195                 200                 205

Val Ser Trp Pro Ser Pro Pro Leu Tyr Pro Leu Ser Pro Ser Cys Gly
    210                 215                 220

Tyr Arg Gln His Phe Pro Ala Pro Thr Ala Ala Pro Gly Ala Pro Tyr
225                 230                 235                 240

Pro Arg Phe Thr His Pro Ser Leu Met Leu Gly Ser Gly Val Pro Gly
```

-continued

```
                245                 250                 255

His Pro Ala Ala Ile Pro His Pro Ala Ile Val Pro Pro Ser Gly Lys
            260                 265                 270

Gln Glu Leu Gln Pro Phe Asp Arg Asn Leu Lys Thr Gln Ala Glu Ser
        275                 280                 285

Lys Ala Glu Lys Glu Ala Lys Lys Pro Thr Ile Lys Lys Pro Leu Asn
    290                 295                 300

Ala Phe Met Leu Tyr Met Lys Glu Met Arg Ala Lys Val Ile Ala Glu
305                 310                 315                 320

Cys Thr Leu Lys Glu Ser Ala Ala Ile Asn Gln Ile Leu Gly Arg Arg
                325                 330                 335

Trp His Ala Leu Ser Arg Glu Glu Gln Ala Lys Tyr Tyr Glu Leu Ala
            340                 345                 350

Arg Lys Glu Arg Gln Leu His Met Gln Leu Tyr Pro Gly Trp Ser Ala
        355                 360                 365

Arg Asp Asn Tyr Gly Lys Lys Lys Arg Arg Ser Arg Glu Lys His Gln
    370                 375                 380

Glu Ser Thr Thr Asp Pro Gly Ser Pro Lys Lys Cys Arg Ala Arg Phe
385                 390                 395                 400

Gly Leu Asn Gln Gln Thr Asp Trp Cys Gly Pro Cys Arg Arg Lys Lys
                405                 410                 415

Lys Cys Ile Arg Tyr Leu Pro Gly Glu Gly Arg Cys Pro Ser Pro Val
            420                 425                 430

Pro Ser Asp Asp Ser Ala Leu Gly Cys Pro Gly Ser Pro Ala Pro Gln
        435                 440                 445

Asp Ser Pro Ser Tyr His Leu Leu Pro Arg Phe Pro Thr Glu Leu Leu
    450                 455                 460

Thr Ser Pro Ala Glu Pro Ala Pro Thr Ser Pro Gly Leu Ser Thr Ala
465                 470                 475                 480

Leu Ser Leu Pro Thr Pro Gly Pro Pro Gln Ala Pro Arg Ser Thr Leu
                485                 490                 495

Gln Ser Thr Gln Val Gln Gln Gln Glu Ser Gln Arg Gln Val Ala
            500                 505                 510
```

(2) INFORMATION FOR SEQ ID NO:10:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:10:

```
Ser Tyr Leu Asp Ser Gly Ile His Ser Gly Ala Thr Thr Thr Ala Pro
 1               5                  10                  15

Ser Leu Ser Gly
            20
```

(2) INFORMATION FOR SEQ ID NO:11:

(i) SEQUENCE CHARACTERISTICS:
(A) LENGTH: 21 amino acids
(B) TYPE: amino acid
(C) STRANDEDNESS: single
(D) TOPOLOGY: linear (ii) MOLECULE TYPE: None -continued (xi) SEQUENCE DESCRIPTION: SEQ ID NO:11:

```
Ser Tyr Leu Gly Asp Ser Gly Ile His Ser Gly Ala Val Thr Gln Val
 1               5                   10                  15

Pro Ser Leu Ser Gly
            20
```